(12) United States Patent
Heath et al.

(10) Patent No.: US 7,776,616 B2
(45) Date of Patent: Aug. 17, 2010

(54) APPARATUSES AND METHODS FOR ISOLATING NUCLEIC ACID

(75) Inventors: Ellen M. Heath, Livermore, CO (US); Ruth M. Shuman, Minnetonka, MN (US)

(73) Assignee: Qiagen North American Holdings, Inc., Germantown, MD (US)

( * ) Notice: Subject to any disclaimer, the term of this patent is extended or adjusted under 35 U.S.C. 154(b) by 1387 days.

(21) Appl. No.: 10/937,746

(22) Filed: Sep. 9, 2004

(65) Prior Publication Data

US 2005/0191760 A1 Sep. 1, 2005

Related U.S. Application Data

(63) Continuation of application No. 09/154,830, filed on Sep. 17, 1998, now abandoned.

(60) Provisional application No. 60/059,152, filed on Sep. 17, 1997.

(51) Int. Cl.
  *G01N 1/14* (2006.01)
  *G01N 1/40* (2006.01)
  *G01N 35/02* (2006.01)
  *G01N 33/50* (2006.01)
  *C12Q 1/68* (2006.01)

(52) U.S. Cl. .................. 436/178; 422/68.1; 422/81; 422/100; 422/101; 435/6; 435/270; 436/49; 436/54; 436/63; 436/94; 436/180

(58) Field of Classification Search ................ 422/64, 422/68.1, 72, 81, 100–102; 435/6, 270, 283.1; 436/47–49, 54, 63, 175, 177–178, 180, 528, 436/94; 536/25.4–25.41
See application file for complete search history.

(56) References Cited

U.S. PATENT DOCUMENTS

| | | | |
|---|---|---|---|
| 4,138,474 A * | 2/1979 | Updike .................... 436/535 |
| 4,151,254 A * | 4/1979 | Gimovsky .................. 422/71 |
| 4,160,803 A * | 7/1979 | Potts ......................... 422/101 |
| 4,214,993 A * | 7/1980 | Forsythe et al. .......... 210/282 |
| 4,234,317 A * | 11/1980 | Lucas et al. ............... 436/71 |
| 4,254,082 A * | 3/1981 | Schick et al. .............. 422/55 |
| 4,270,921 A * | 6/1981 | Graas ........................ 436/67 |
| 4,341,635 A * | 7/1982 | Golias ....................... 210/656 |
| 4,430,496 A | 2/1984 | Abbott |
| 4,531,088 A * | 7/1985 | Czaban et al. ............ 324/71.1 |
| 4,539,855 A * | 9/1985 | Jacobs .................... 73/864.25 |
| 4,675,299 A * | 6/1987 | Witty et al. .............. 436/165 |
| 4,751,186 A * | 6/1988 | Baisch et al. .............. 436/47 |
| 4,766,082 A * | 8/1988 | Marteau D'Autry ...... 436/178 |
| 4,775,629 A * | 10/1988 | Kuhl et al. ................ 422/101 |
| 4,787,971 A * | 11/1988 | Donald .................... 210/198.2 |
| 4,863,610 A * | 9/1989 | Campbell ................. 210/658 |
| 4,935,342 A | 6/1990 | Seligson et al. |
| 4,997,932 A | 3/1991 | Reardon et al. |
| 5,038,852 A | 8/1991 | Johnson et al. |
| 5,057,426 A | 10/1991 | Henco et al. |
| 5,085,781 A * | 2/1992 | Tsuru et al. .............. 210/692 |
| 5,106,761 A | 4/1992 | Kuniyuki |
| 5,147,608 A * | 9/1992 | Hudson et al. .............. 422/63 |
| 5,187,083 A | 2/1993 | Mullis |
| 5,202,093 A * | 4/1993 | Cloyd ....................... 422/102 |
| 5,234,809 A | 8/1993 | Boom et al. |
| 5,234,824 A | 8/1993 | Mullis |
| 5,260,028 A * | 11/1993 | Astle .......................... 422/81 |
| 5,308,506 A | 5/1994 | McEwen et al. |
| 5,358,641 A * | 10/1994 | Sanford et al. ............ 210/656 |
| 5,368,729 A * | 11/1994 | Stefkovich et al. ........ 210/266 |
| 5,395,521 A * | 3/1995 | Jagadeeswaran ........ 210/198.2 |
| 5,405,951 A | 4/1995 | Woodard |
| 5,439,593 A * | 8/1995 | Price ........................ 210/660 |
| 5,443,791 A * | 8/1995 | Cathcart et al. ............ 422/65 |
| 5,446,263 A | 8/1995 | Eigen et al. |
| 5,460,968 A | 10/1995 | Yoshida et al. |
| 5,531,959 A * | 7/1996 | Johnson et al. ............ 422/70 |
| 5,538,849 A | 7/1996 | Uematsu et al. |
| 5,585,068 A | 12/1996 | Panetz et al. |
| 5,585,070 A * | 12/1996 | Lessard et al. ............ 422/101 |
| 5,595,653 A * | 1/1997 | Good et al. ................ 210/289 |
| 5,599,667 A | 2/1997 | Arnold, Jr. et al. |

(Continued)

FOREIGN PATENT DOCUMENTS

EP 819696 A2 1/1995

(Continued)

OTHER PUBLICATIONS

Hawkins et al., "DNA Purification and Isolation Using a Solid-Phase", Nucleic Acids Research, 22, 4543-4544 (1994).

*Primary Examiner*—Arlen Soderquist
(74) *Attorney, Agent, or Firm*—Seed IP Law Group PLLC

(57) ABSTRACT

The present invention is an apparatus and method for purifying and isolating nucleic acid. The system uses one or more automated stations to perform steps of the method, including loading a sample onto a solid support in a processing container, purifying the sample, and isolating nucleic acid from the sample. A pump or vacuum may be used in the apparatus of the present invention for supplying fluids to the sample. A pump, vacuum or centrifuge may be used to separate impurities from the sample or to separate nucleic acid from the solid support. Exemplary solid supports and sample processing containers are disclosed.

9 Claims, 15 Drawing Sheets

U.S. PATENT DOCUMENTS

| | | | |
|---|---|---|---|
| 5,620,898 A | | 4/1997 | Yaremko et al. |
| 5,652,141 A | | 7/1997 | Henco et al. |
| 5,683,916 A | | 11/1997 | Goffe et al. |
| 5,736,100 A | | 4/1998 | Miyake et al. |
| 5,747,350 A | * | 5/1998 | Sattler ................ 436/180 |
| 5,804,684 A | | 9/1998 | Su |
| 5,807,527 A | | 9/1998 | Burgoyne |
| 5,833,860 A | * | 11/1998 | Kopaciewicz et al. ....... 210/650 |
| 5,846,492 A | * | 12/1998 | Jacobs et al. ............. 422/67 |
| 5,855,852 A | | 1/1999 | Bienhaus et al. |
| 5,874,004 A | * | 2/1999 | DeWitt ................ 210/634 |
| 5,919,356 A | * | 7/1999 | Hood .................. 210/85 |
| 5,973,137 A | | 10/1999 | Heath |
| 5,985,215 A | | 11/1999 | Sakazume et al. |
| 6,054,039 A | | 4/2000 | Shieh |
| 6,110,428 A | | 8/2000 | Borst et al. |
| 6,117,398 A | | 9/2000 | Bienhaus et al. |
| 6,218,531 B1 | | 4/2001 | Ekenberg |
| 6,530,288 B1 | * | 3/2003 | August et al. ............. 73/863.31 |
| 6,566,145 B2 | * | 5/2003 | Brewer ................. 436/178 |
| 7,115,719 B2 | | 10/2006 | Paulsen |
| 7,148,343 B2 | | 12/2006 | Bair, Jr. et al. |
| 2001/0000149 A1 | | 4/2001 | Smith et al. |
| 2003/0068830 A1 | | 4/2003 | McCoskey et al. |
| 2003/0073830 A1 | | 4/2003 | Heath et al. |
| 2004/0019196 A1 | | 1/2004 | Bair et al. |
| 2005/0032105 A1 | | 2/2005 | Bair et al. |
| 2005/0171333 A1 | | 8/2005 | Paulsen |
| 2006/0105372 A1 | | 5/2006 | Bair et al. |
| 2007/0043216 A1 | | 2/2007 | Bair, Jr. et al. |

FOREIGN PATENT DOCUMENTS

| | | |
|---|---|---|
| WO | WO 95/02049 | 1/1995 |
| WO | WO 96/18731 | 6/1996 |
| WO | WO 99/13976 | 3/1999 |
| WO | WO 99/39009 | 8/1999 |
| WO | WO 99/39010 | 8/1999 |
| WO | WO 03/033739 | 4/2003 |
| WO | WO 2004/094635 | 11/2004 |
| WO | WO 2005/058933 | 6/2005 |

* cited by examiner

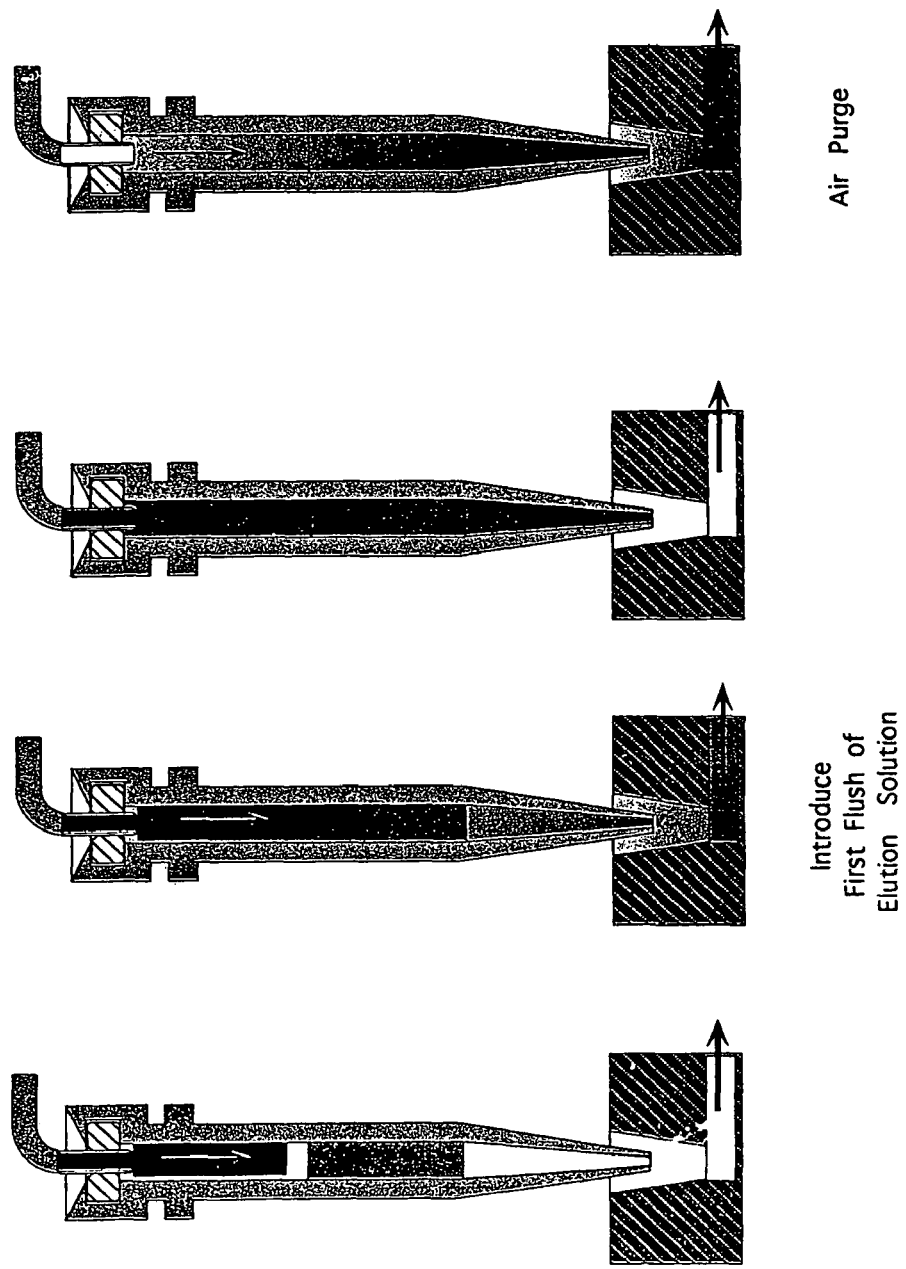

Optional protocol (preferred embodiment): heat column after conditioning to c. 90°C, for approx. 5 minutes, then instill elution solution, optionally prewarmed, then, optionaly mix while continuing heating to continue elution step.

Figure 5b

Mixing step: in order to enhance elution of n.a., a mixing procedure is desirable:

1. induce fluid motion thru the column by alternately aspirating and dispensing small volume of fluid. Volume to be such that the fluid column remains within the head space provided above and below the solid phase

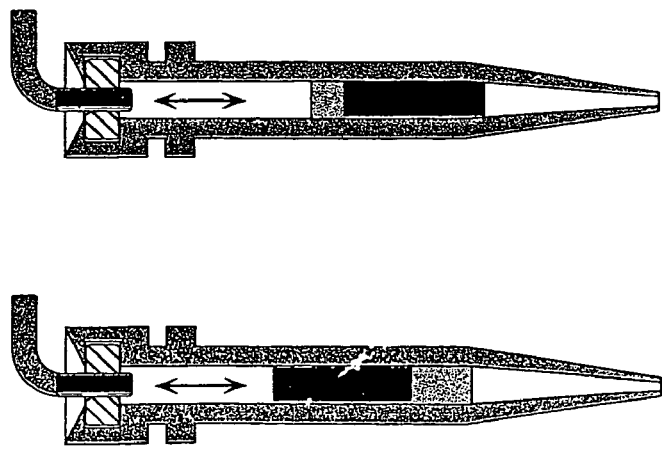

Induce fluid motion by relatively high frequency displacement of septum: mechanical displacement of about one millimeter at a frequency of between 20 to 120Hz produces small displacements of the fluid column within the device and highly effective mixing.

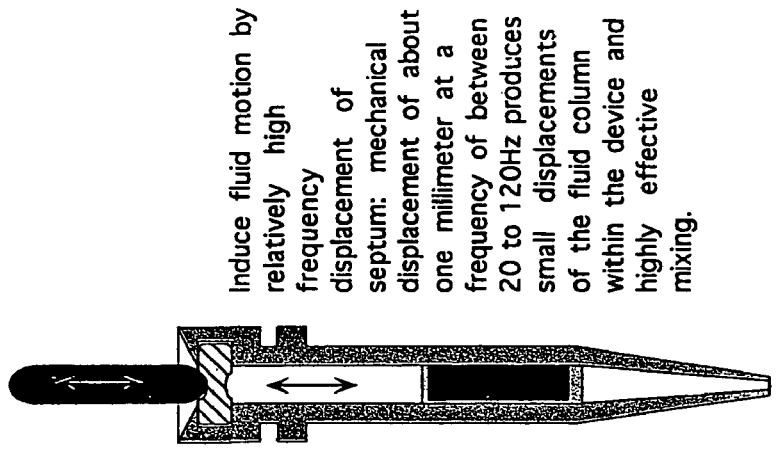

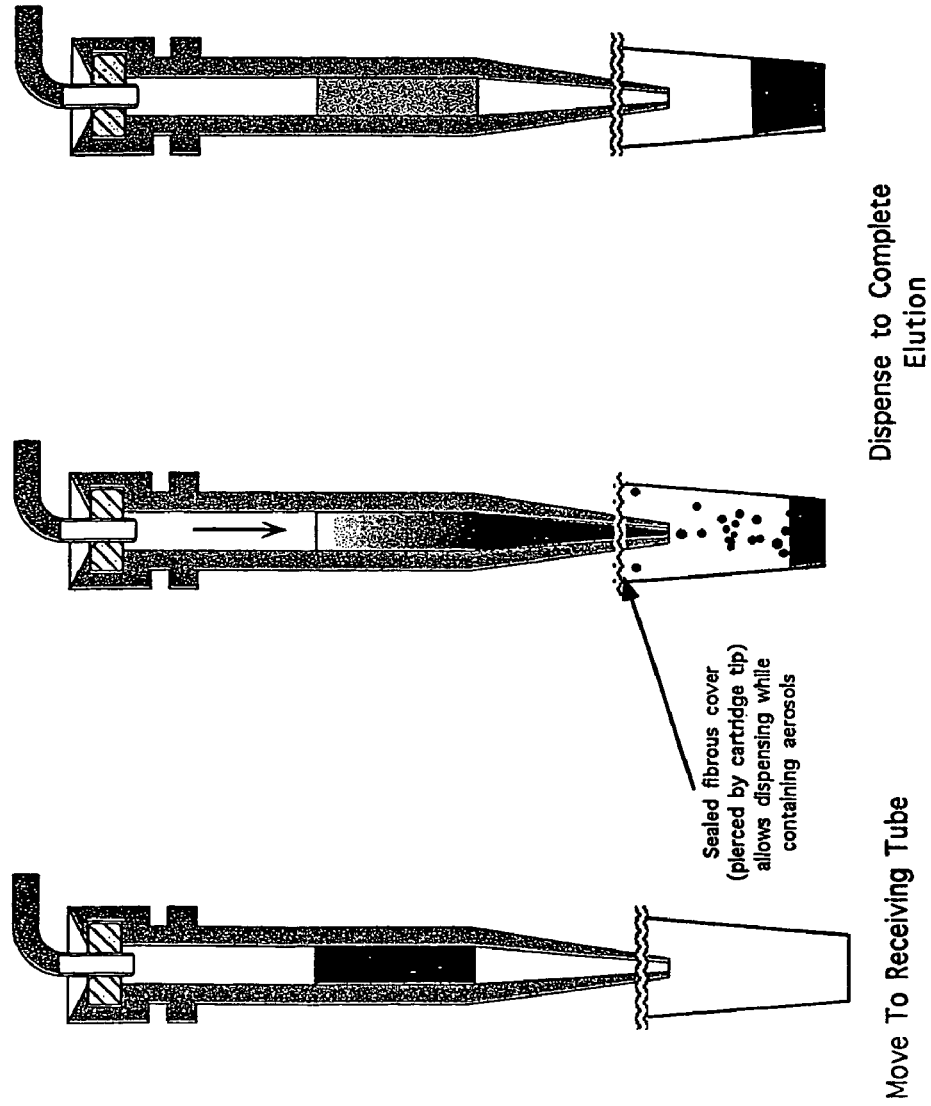

Optional: Precision Aliquot

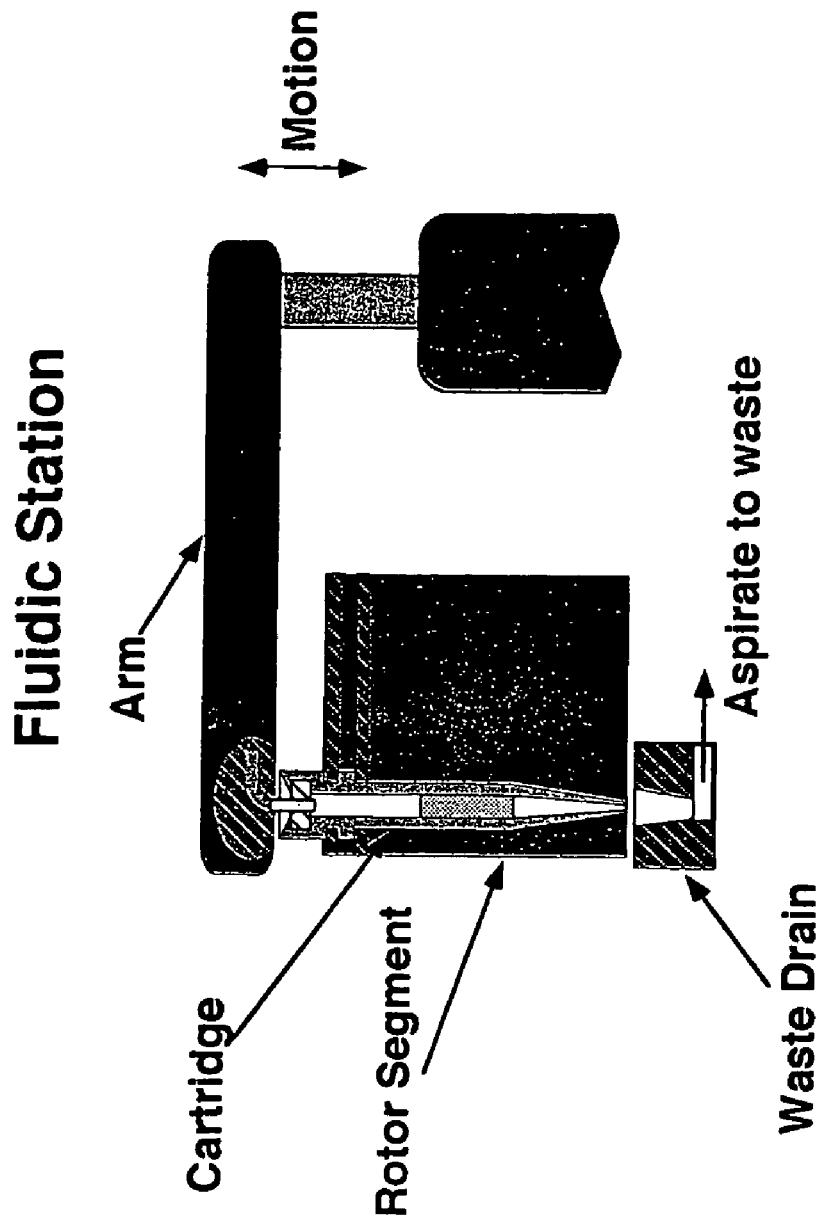

Sample Collection Tube

APPARATUSES AND METHODS FOR ISOLATING NUCLEIC ACID

CROSS-REFERENCE TO RELATED APPLICATIONS

This application is a continuation of application Ser. No. 09/154,830, filed Sep. 17, 1998, now abandoned, which claims the benefit of U.S. Provisional Application Ser. No. 60/059,152 filed Sep. 17, 1997, now expired. Application Ser. No. 09/154,830 and Application Ser. No. 60/059,152 are incorporated by reference herein.

BACKGROUND OF THE INVENTION

The invention is an apparatus and method for isolating nucleic acid from a biological sample.

1. Field of the Invention

The invention relates to the field of nucleic acid isolation and to the field of automated processing systems.

2. Description of Related Art

Nucleic acid isolation from biological sources or reactions is an important step in performing many diagnostic tests and biological studies. Prior art manual methods and systems for isolating nucleic acid have been tedious and time-consuming. What is needed is a system for automating the process of nucleic acid isolation.

SUMMARY OF THE INVENTION

The present invention provides a method and apparatus for automating the process of isolating nucleic acid.

BRIEF DESCRIPTION OF THE DRAWINGS

FIG. 4 shows a representative example of the sample, sample processing container and wash solution as used in the isolating step of the present invention, where the sample processing container is hushed and conditioned.

FIG. 5b) shows a representative example of an optional process of mixing the sample solid support and elution solution in the isolating step of the present invention.

FIG. 6 shows a representative example of dispensing the elution solution which contains nucleic acid of the present invention.

FIG. 9 shows a representative example of a fluidic station of the present invention.

DESCRIPTION OF THE PREFERRED EMBODIMENT(S)

Figure 1:
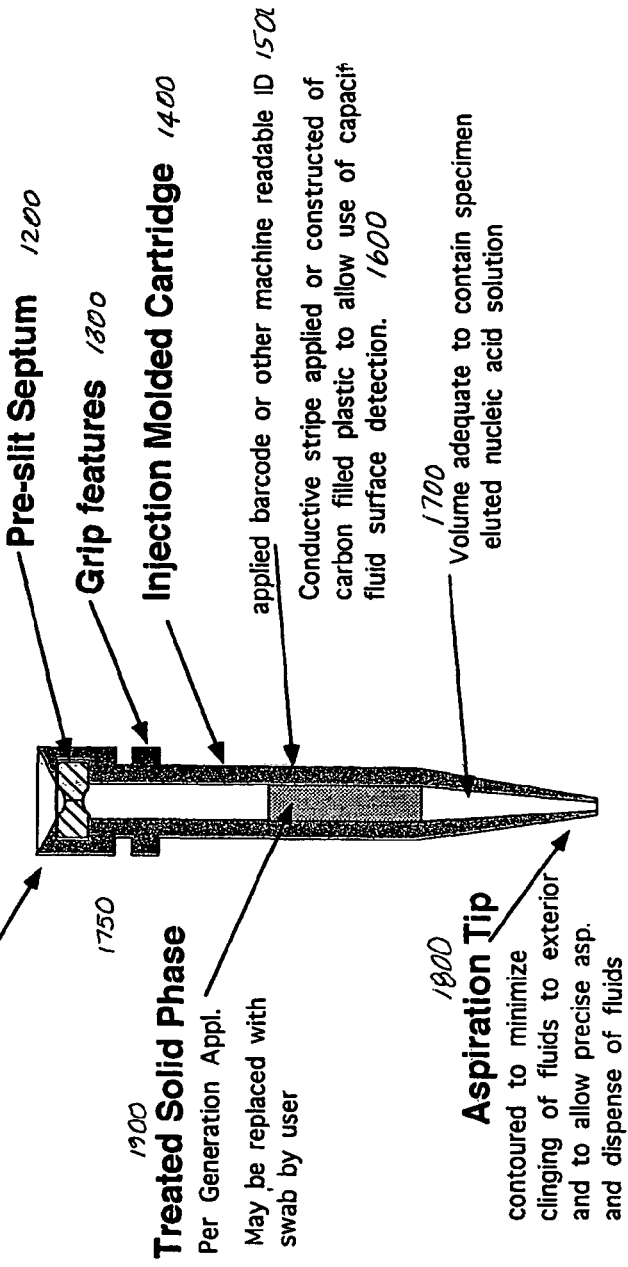
FIG. 1 is a representative example of a sample processing container of the present invention.

The invention relates to a method and apparatus for purifying and isolating nucleic acid.

1. Process for Isolating and Purifying Nucleic Acids.

For the general method of the present invention, the first step is to obtain a biological sample. The biological sample may be blood or a fluid containing nucleic acid. The second step is to apply the sample to a solid support. Nucleic Acids bind to the solid support while impurities such as cell membranes, proteins, and lipids are washed off the solid support by one or more reagents. The purified nucleic acid is then removed from the solid support and becomes ready to be processed further.

The sample, from which nucleic acid is to be isolated, is applied to any solid support. The nucleic acid from the sample binds to the solid support, and remains on the solid support when a purification/wash solution is added to the solid support. However, the impurities present in the sample, such as proteins, carbohydrates, lipids, and other components, are washed away from the solid support by a purification/wash solution.

One type of solid support is a cotton swab (Hardwood Products, Guilford, Me.), which is useful for obtaining biological samples such as epithelial cells from the inner cheek or body fluids. Another type of solid support is a piece of cellulose paper, which may be obtained from a sheet of cellulose paper by cutting one portion of the paper. A polyolefin solid support may be obtained by cutting a small section out of a sheet of polyolefin or by cutting a section from a solid chunk of polyolefin. In the present invention, Polyolefin is preferred because Polyolefin binds more sample cellulose paper or cotton swabs. For example, a polyolefin solid support may be used to support 200 µL of blood, while a piece of cellulose paper may support only 25 µL of blood.

Other suitable solid supports exist and are well known to those in the art. For example, materials which comprise or consist of the following are adequate solid supports: cellulose, cellulose acetate, glass fiber, nitrocellulose, nylon, polyester, polyethersulfone, polyolefin, polyvinylidene fluoride, and combinations thereof. Other materials which are well known to those skilled in the art, can be used.

A sample containing large numbers of cells or organisms is first contacted with the solid support and lysed. Lysing may be done by the addition of a preferred Lysing solution (Gentra Systems, Inc., Minneapolis, Minn.), or by contacting the cells with a solid support preheated with a Lysing solution.

After applying the sample to the solid support, the sample is purified by removing impurities, while leaving the nucleic acid on the solid support. The purification step may employ a series of wash steps using a purification solution, otherwise known as a "wash" solution. This solution removes the impurities from the solid support without removing the nucleic acid from the solid support. Typically, the wash solution is a reagent comprising a detergent of low ionic strength, a buffer, a chelating reagent, and a salt at a low concentration.

There are several suitable wash solutions well known to those skilled in the art. A preferred wash solution is Generation DNA Purification Solution® (Gentra Systems, Inc., Minneapolis, Minn.).

The purification step may also involve a step of separation, which involves the application of force to the solid support to remove any residual impurities from solid support. Separation may be performed, for example, by a centrifuge/microfuge, gravity flow, positive pressure, air flow, vacuum (negative) pressure, or by mechanical agitation.

Purification may also involve multiple applications of the wash solution. Preferably, at least two wash steps are performed and at least two separation steps are performed.

After the solid support has been washed, the nucleic acid must be removed or isolated from the solid support. To isolate the nucleic acid from the solid support, an elution solution is added to the nucleic acid. The elution solution causes the nucleic acid which is attached to the solid support to separate from the solid support, thereby causing the nucleic acid to flow to an area where it may be collected. Depending on the type of elution solution used, it may be necessary to heat the solid support in order to increase the efficiency of the elution solution.

There are several suitable elution solutions and are well known to those skilled in the art. A preferred elution solution is Generation DNA Electron Solution® (Gentra Systems, Minneapolis, Minn.).

After successive washes with elution solution, the nucleic acid is collected. This is accomplished by the use of a centrifuge/microfuge, positive pressure, gravity flow, or a vacuum applied to one side of the solid support. The collecting step causes the nucleic acid to flow from the sample processing container into a collection area.

While nucleic acid isolation and purification may be performed manually, automated processing is desired to obtain purified nucleic acid from a large number of samples, to speed up the isolation/purification process, and to decrease the probability of human error.

2. Automated Apparatus for Nucleic Acid Purification.

The present invention relates to a method and apparatus which automatically isolates and purifies nucleic acid according to the steps as previously discussed.

Generally, the automated apparatus should perform many functions, including loading the biological sample (such as blood) onto a solid support, and placing the solid support into a sample processing container, purifying, isolating, collecting and dispensing. The sample may be loaded directly on to a solid support prior to placing it in a sample processing container or both sample and solid support may be loaded concurrently.

Suitable samples include any material containing nucleic acid. Specifically, biological materials such as eukaryotic cells, prokaryotic cells, viruses, lysates, and homogenates thereof. Sources of biological material include, for example, body fluids, wastes, and excretions.

Suitable sample processing containers include centrifuge tubes, spin tubes, syringes, cartridges, chambers, multiple-well plates, test tubes, and combinations thereof. Other suitable containers are envisioned.

The loading step is optional in the automated apparatus, because loading may be easily performed by a lab technician. For example, a lab technician may swab a patient's cheek with a cotton swab, cut the swab into a smaller size, and then place the cotton swab into a test tube or other processing container. An apparatus for automatically placing the solid support into a processing container and loading the sample into the processing container (and thus onto the solid support) is described below.

The next step is to purify the sample on the solid support. This step includes the steps of washing the sample on the solid support (by applying a wash/purification solution) to release the impurities from the sample, separating at the impurities from the solid support, and may include collecting the waste (the separated impurities). This step may be repeated to ensure that all (or most of) the impurities are removed from the sample.

After the step of purification, the nucleic acid can be isolated from the solid support by the automated apparatus. First, the nucleic acid is released from the solid support by adding elution solution to the solid support/sample, and optionally adding a heating step. A separation process is used again to force the nucleic acid released from the solid support to a collection area. The collected nucleic acid is purified and preferably in a concentration suitable for performing further processes.

The automated apparatus is then ready to begin processing new samples.

Each of the functions may be performed by a station in the automated apparatus. Thus, a loading station may place the sample onto a solid support in a processing container. A purification station may wash the sample, separate the waste from the solid support, and collect the waste. An isolation station may elute the solid support, heat the solid support, and separate the nucleic acid from the solid support into a collection area. The apparatus can then be reset manually or by a process a new set of samples.

Alternatively, one station may be used to perform all the steps, where different machine components are used to effect the desired operation. In this type of apparatus, a pump may force wash solution through a solid support, and waste may be collected in a waste collection vessel below the solid support. When washing is complete, the same pump may pump elution solution into the solid support and apply heat using a heating device. Next, gas may be pumped through the solid support, using the same pump, to collect the sample in a different collection vessel which has replaced the waste collection vessel.

Combinations of stations may be used, for example, a loading station may be used in conjunction with a station that performs the purification and isolation steps. A loading station may also be used in conjunction with a purifying, isolating and collecting apparatus.

Preferably the automated apparatus is under the control of a microprocessor running suitable software. This enables monitoring and recordkeeping of the processed samples, and increases the ease of operation. Different embodiments of the invention may utilize different mechanical devices for performing the separation step. Preferred devices include a pressure pump, vacuum pump and centrifuge/microfuge. In one embodiment, the separation device used in the purification step is the same as the separation device used in the isolation step.

3. Apparatus/Station for Loading Samples and Solid Support.

A system for loading a solid support and sample containing nucleic into a processing container may comprise one "station" of the apparatus, or may be integrated into other stations. Alternatively, the system for loading may be moved into place when required. In that embodiment, it is unnecessary to move sample processing containers at all.

A processing container carrier preloaded with sample processing containers can be brought into position to receive a solid support from a dispensing apparatus. Preferably, a conveyor belt or robotic arm is used to bring the processing container carrier into position. However, a robotic manipulator arm or a rotor (not shown) may be used to bring the sample to the sample processing container. A sensor, which may be mechanical, electrical, electro-optical, magnetic, etc., or any other well-known sensor type, determines that the processing container carrier is in the correct position, and informs a microprocessor (not shown), which stops the conveyor belt.

In one embodiment of the present invention, the sample must be added to the solid support. Automated pipets may be used to dispense the sample, onto, into the sample processing containers. The pipets obtain the sample from sample source containers which are located in a source carrier. For example, at least one sensor detects when the sample processing container carrier and source carrier are in position. The source carrier sensor is for example, an electro-optical sensor. Conveyor belts can be used to bring the carriers into position. The pipets may be positioned to move between the sample source containers and the sample processing containers. The pipets may be inserted into the sample source containers and the sample processing containers by moving the pipets into position and then moving the conveyor belts vertically. Alternatively, the rails supporting the pipets may be moved vertically, for example, by a telescoping stand.

Other methods of obtaining the sample may be used, for example, by connecting a tube to the sample source containers and pumping the sample into the sample processing containers. Moreover, one may aspirate the sample from the sample cell container to the sample processing container. Furthermore, the sample cell container itself may comprise an aspirating tip, which may allow non-automated or automated aspiration directly into the sample processing container. In addition to pipetting, aspirating, and pumping directly into the sample processing container, one may pipette, aspirate, and pump directly onto the solid support.

The sample processing container or the sample container may contain a machine readable code for identifying the sample, the type of solid support, the patient's identification code, or any pertinent facts regarding nucleic acid separation. Machine readable code may be, for example, a bar code. Machine readable codes may be read by electrical, mechanical, optical, and magnetic scanning devices. Thus, the apparatus of the present invention has a means for identifying and recordkeeping.

After the sample is inserted onto the solid support within the sample processing container, the sample processing container may be prepared for the subsequent processing steps. This may entail attaching appropriate coverings and/or tubing to the sample processing container so that the wash fluid and elution solution can be easily added to the solid support within the sample processing container. A robotic manipulator arm may be used for such procedures.

For example, a cover positioning station or apparatus may be operated to bring a cover with a tube into position over the sample processing container. The cover may be, for example, a stopper with tubing or may be a snap-fit cover with tubing. The cover may have a groove, flange or tab to enable it to be grasped by a robotic manipulator. A machine readable code may also be placed on the cover.

When the cover is placed on the sample processing container, the containers are ready to be connected to a purification apparatus, or to be transferred to a purification station.

Microprocessor control provides a means for measuring volumes of the sample taken from a sample container. For example, when an aspirator is used, well known relationships between gas and volume and temperature at a given pressure may be used to obtain precise volumes of the sample. Moreover, microprocessor control may alarm the user when the volumes of the sample in a sample container become inadequate. For example, if the sample is a liquid, then electronic circuit may be able to tag changes in capacitance when a liquid level becomes inadequate. If the liquid level were to become inadequate in this example, then the microprocessor may be able to interrupt the loading of the sample into the sample cell container.

4A. Apparatus/Station for Purifying Sample/Solid Support.

An apparatus or station for purifying the sample on the solid support, previously placed in a sample processing container may include, for example, a control unit containing a microprocessor. The control unit is connected to at least one sensor, valves, a pump, and a motor to control the positioning of a waste carrier. The apparatus contains a number of valves used to channel liquids or gas through the pump. The pump is preferably a peristaltic pump or other pump suitable for pumping small quantities of liquid and gas through tubing.

The outlet of the pump is connected to the inlet of number of sample processing containers. Each of the processing containers may have an outlet disposed directly above a waste container. The waste containers may be positioned on the waste carrier. The waste carrier may be moved into position via a conveyor belt or rotor, and sensor. Alternatively, the waste containers may not enclose the outlet of the processing containers, but may be directly below the outlets. This negates the need for moving the waste containers. However, there is no need for separate waste containers. A waste trough may be used to collect the waste from all the sample processing containers.

In operation, for example, the control unit first causes a valve associated with wash solution (stored in a wash solution reservoir) to be opened. The control unit may turn on the pump, pumping wash solution into each of the sample processing containers. The wash solution flows into the sample processing containers, removing impurities from the solid support. This performs the wash step.

After a predetermined amount of time, the control unit closes the wash solution valve. The control unit may wait for another predetermined amount of time prior to performing another action in order to allow the wash solution to soak into the solid support.

Next, the control unit opens the valve associated with a gas input. Gas is then pumped through the sample processing containers, forcing the wash solution through the bottom of the sample processing containers and into the waste containers. This performs the separation step, where the waste separated from the solid support by the wash solution is forced out of the sample processing container to be collected in the waste containers.

It may be necessary to repeat the wash/separation steps a number of times to ensure that a majority of the impurities are removed from the solid support. This is easily accomplished by repeating the process previously described as many times as necessary, preferably at least two times. That is, the control unit closes the gas valve and reopens the wash solution valve. When sufficient wash solution is pumped into the sample processing containers, the wash solution valve is closed and the gas valve is opened. Gas then forces the wash solution and impurities into the waste containers. It is a simple matter to repeat this process as many times as desired.

As described earlier, microprocessor control allows one to measure the volume of the sample, the wash solution, and the volume of gas. Moreover, microprocessor control may alert the user when these volumes become inadequate to continue processing, or interrupt the purification process in such an instance.

4B. Loading Sample Processing Containers onto the Purification Apparatus.

For example, the sample processing containers may be connected to tubing in the purification apparatus/station. In order to connect the sample processing containers in this way, the sample processing container carrier is moved into a predetermined position with aid of sensors. The sample processing containers contain an inlet and outlet. The inlet and/or outlet may be preconnected or may be automatically connected.

To connect the sample processing container to the purification apparatus, the sample processing container carrier which holds the sample processing container may be moved into position below the tubing of the purification apparatus. The correct position is determined via a sensor connected to the control unit. Once the carrier is in position, either the purification apparatus or the carrier is moved to establish a connection between the tubing and the inlet of the sample processing container. For example, a conveyor belt is moved vertically to engage the inlet of the sample processing container and the tubing of the purification apparatus.

After a connection is established, the sample processing container carrier is moved away and a waste carrier is brought into position, which is once again sensed by the sensor in communication with the control unit.

To remove the sample processing containers, the sample processing container carrier is once again translated into position, either horizontally and/or vertically. The sample processing containers may then be removed from the tubing, and placed into the sample processing container carrier. This removal may be performed, for example, by retracting the tubing into the housing of the purification apparatus or by using a robotic manipulator arm. If rotational coupling is used, the sample processing container may be connected and unconnected via a rotational force applied from a manipulator.

After removal, the sample processing container carrier and sample processing containers are moved to the next station or the next apparatus is brought into operation. The next apparatus/station isolates the nucleic acid from the solid support.

5. Apparatus/Station for Isolating Nucleic Acid from Solid Support.

The solid support which has been washed and undergone separation contains nucleic acid bound to the solid support, but without significant impurities. The nucleic acid is ready for removal from the solid support.

An isolating apparatus may be combined with the purification apparatus/station described previously, but may be provided in another station if desired. Another reservoir is connected to a valve in communication with the control unit. The second reservoir holds elution solution, which is a solution that removes nucleic acid from the solid support. A heater is also controlled by the control unit. The heater may be used to increase the efficiency of the elution solution. The sample processing containers may be located in a thermally insulated chamber, which makes the heating of the sample processing containers more efficient.

After the final gas separation step, where gas is used to force the wash solution through the sample processing container, waste may be collected in the waste containers. The waste containers may then be removed by appropriate means.

Once the collection containers are positioned, the gas valve is closed and the valve associated with the elution solution is opened. The pump is activated to pump in a predetermined amount of elution solution onto the solid support within the sample processing containers.

The elution solution may need time to release the nucleic acid from the solid support, thus the control unit may wait for a predetermined amount of time prior to opening the gas valve and activating the pump to force the elution solution with the isolated nucleic acid from the sample processing containers and into the collection containers.

In order to reduce the amount of time necessary for the elution solution to release the nucleic acid from the solid support, a heating unit is preferably used. However, ultrasound or microwave energy may also be used. After applying elution solution to the solid support, the heater is activated. Preferably, the system is set up to allow the elution solution to reach a temperature of at least 60° C. To achieve the desired temperature, the heater may be activated for a predetermined amount of time, or until a thermocouple detects a predetermined temperature. Preferably, the sample processing containers are contained within a thermally insulated chamber, allowing the sample processing containers to rapidly gain in temperature.

After determining that subsequent heating is unnecessary, a control unit turns off the heater and opens the gas valve, closing all other valves. At this point, the nucleic acid is separated from the solid support. Pumped gas forces the elution solution containing the purified nucleic acid into the collection containers.

The collection carrier may then be sent on for further processing. In one embodiment, the collection containers and the isolated nucleic acid are advanced to the next station by mechanical means. Alternatively, another apparatus may be brought into proximity of the collection containers and/or collection carrier.

Automated measuring of volumes may be done by microprocessor control as discussed previously. Moreover, an alarm may be triggered when volumes become inadequate, or for any other reason that the microprocessor may be preprogrammed to determine.

6. Apparatus/Station(s) for Purification and Isolation Via Vacuum.

Alternatively, a vacuum system may be used to force the wash solution and the elution solution, through the sample processing containers.

Alternatively, the wash solution and the elution solution may be gravity fed into the sample processing containers, and forced out of the containers via vacuum force.

Vacuum processing is useful to purify and isolate a large number of samples. In a high-throughput system, for example, a vacuum plate is used to process 96 or more samples at a time. In this system, individual sample processing containers are not used; rather, a single processing plate containing 96 or more solid supports and chambers is used.

In operation, wash solution is pumped into the cartridges. The vacuum is operated to create a pressure differential between the inside of the chamber and the exterior of the chamber. This causes the waste to flow into a waste collection platform.

EXAMPLES

Example 1

An Integrated Sample Processing Cartridge

One embodiment of the sample processing container is a sample processing cartridge 1000. An integrated sample processing cartridge is designed to achieve the following objectives:

(i) The extraction and purification of nucleic acids from biological samples including, but not limited to, cell culture suspensions, eukaryotic cells, prokaryotic cells, viruses, lysates, etc., whole blood and preparations thereof, and other body fluids, wastes, excretions, etc.
(ii) The enablement of the ready automation of nucleic acid purification and isolation from the biological samples described above.
(iii) The enablement of the direct transfer of the samples described above into the chamber of the sample processing cartridge 1450 and, thereby, onto the solid support or capture matrix 1900.
(iv) The introduction of required reagents and solutions needed to perform the purification and isolation of nucleic acids.
(v) The enablement of the precise dispensation of solution containing relatively purified and isolated nucleic acids after the purification and isolation steps.
(vi) The purification and isolation of nucleic acids from samples contained on swabs.

The objects of the invention are achieved by providing a sample processing cartridge 1000 composed of an injection molded cartridge-like device having an open end adapted to the aspiration of fluids through an aspiration tip 1800; a generally tubular body 1400 constructed to have an adequate volume to contain a solid support, capture column or lysing matrix 1900 as described in co-pending U.S. patent application Ser. No. 09/017,218, and subsequently contains process fluids such as a purification or wash solution, elution solution, etc.; a closed end 1100 comprised of a sealed top 1150, a septum 1200 which may be slit, pierced or otherwise constructed so as to allow fluid communication with an external fluid circuit 2100 while maintaining an hermetic seal of the given end of the cartridge at all times and incorporating flexibility adequate to allow external mechanical stimulation of fluid motion within the chamber of the cartridge 1450; an external retention or grip feature consisting of at least one ridge or groove allowing ready manipulation by an automated or robotic device; labeling features consisting of a machine readable 10 code, such as a bar code, allowing unique identification of each individual cartridge by an automated scanning device. The cartridge is constructed of materials compatible with the isolation of nucleic acids. Additionally, the cartridge is constructed with relatively thin walls to allow rapid heating as required by the process purification and isolation steps.

The cartridge has the following features. The features are shown in FIG. 1.

1.1. Closed End: The closed end comprises a sealed top 1150, and a septum 1200.

1.1.1 Sealed top 1150: The sealed top 1150 allows the retention of fluids within the cartridge, provides fluid communication with the interior chamber of the cartridge as needed, and provides for the placing of a septum 1200 as shown in Figure. The sealed top and septum are also designed to facilitate easy automation of the introduction of a gas, such as air, nitrogen, and inert gases, or other adequate fluids to displace the elution solution. The introduction of a gas or fluid is important in the isolation of nucleic acids from the solid support or contact matrix since it causes bulk mixing in the solid support or within the fibers of the contact matrix. The addition of the aforementioned mixing step strips the nucleic acids from the fibers and distributes them more uniformly into the bulk fluid, thus enabling more effective nucleic acid recovery. The sealed top 1150 can be constructed as a screw cap or snap fit cap to permit the introduction of cotton swabs, disks, etc. to the chamber of the cartridge in lieu of the solid support or lysing matrix. Alternatively, a tethered, snap or press fit cap could be molded as a unitary feature of the cartridge.

1.1.2 Septum 1200: Fluid is introduced into the body of the cartridge through a septum 1200. The septum maybe pre-slit or pre-pierced the septum is retained by the use of a press fit or bonded retaining ring, by heat staking the upper area of the cartridge, or by direct bonding of the ring. The septum could also be retained in the sealed top 1150. This septum 1200 also facilitates induced fluid motion within the cartridge to substantially enhance mixing within the solid support or capture matrix 1900 and aid in the isolation of nucleic acids after the application of an elution solution. The septum 1200 may be mechanically stimulated by an external device such as a solenoid, motor driven mechanism, etc. The resulting displacement of the septum 1200 allows the movement of the fluid within the cartridge as a bolus. Relaxation of the septum then returns the fluid to the initial position. Rapidly repeating this cycle results in a high fluid shear across the material of the solid support or the fibers of the contact matrix and thus enhances the mixing of the nucleic acid and the elution solution. This greatly increases the recovery of nucleic acid. In cases where the sealed top is a tethered, a snap or press fit cap, the septum would be retained in the cap to provide access to the interior of the cartridge for ready insertion of a cotton swab or other collection means.

1.4. Open End or Inlet: The open end or inlet allows the aspiration of sample in a precise manner while minimizing exterior contamination. This is especially important when the sample is a body fluid such as blood, semen, plasma, or a sterile cell culture sample where exterior contamination affects the quality of the final product. The inlet consists of, essentially, an aspiration tip 1800 and a head space 1700 above the tip. The inlet head space has an adequate volume to contain the sample prior to contact with the solid support or capture matrix 1900. The volume of the head space is also adequate to contain a volume of purified and isolated nucleic acid so as to allow the precise aspiration of the purified and isolated nucleic acid for dispensing subsequent precise aliquots. The aspiration tip 1800 is contoured to minimize the clinging of fluids to the exterior of the cartridge and to allow the precise aspiration and dispensing of fluids.

1.5. Cartridge Body 1400: The main body of the cartridge is injection molded and designed with an aspect ratio that allows it to reach to the bottom of a standard draw tube during the sample loading process. The interior diameters are selected to allow for the maintenance of an intact fluid bolus. In another embodiment of the cartridge design, the cartridge body is designed to fit inside a centrifuge or micro-centrifuge. When isolation and collection of the nucleic acids is performed by centrifugation of the sample processing cartridge, a relatively large amount of energy can be applied to the nucleic acids clinging to the solid support or the fibers of the capture matrix. This improves the overall yields of the isolated and purified nucleic acids. The chamber of the cartridge 1450 has an adequate volume to hold a solid support lysing matrix 1900, and a head space below 1700 and a head space above 1750 the solid support 1900.

1.6. Materials of Construction of the Sample Processing Cartridge: The sample processing cartridge is constructed of materials that are inert, hydrophobic, and that to do not bind to nucleic acids. These construction materials may be, but are not restricted to, polypropylene, polytetrafluoroethylene, high density polyethylene, etc. In another embodiment, carbon or other additives are added to the construction material to allow for the use of conductive or captive level sensing. Conductive or captive level sensing may also be achieved by the addition of a conductive stripe or coating 1600. The conductive stripe or coating may be applied by vapor deposition or other means such as pad printing of conductive inks, ink jet printing, etc.

1.7. Identification Means: The sample processing cartridge is equipped with the addition of a machine readable identification code 1500, such as a barcode, to allow for positive sample tracking and to allow the identification of reagent lot and/or size of cartridge and/or other cartridge specific information.

1.8. Retention or grip features 1300: The sample processing cartridge is designed with a retention or grip feature 1300 consisting of one or more ridges, grooves, or flanges near the sealed top 1100 to allow the reproducible and reliable automated acquisition of cartridge and to facilitate easy handling of the cartridge within the instrument.

1.9. Thin wall construction: The sample processing cartridge has a thin wall to maximize heat transfer rate. This is especially important during the elution process when the solid support or contact matrix needs to be adequately heated for short periods of time.

Example 2

Determining the Performance of a Sample Processing Cartridge to Purify and Isolate DNA and Comparing Centrifugation Vs. Air Flow as Possible Elution Methods To test the performance of the DNA purification device, a sample processing container designed to purify DNA, DNA was purified from whole blood samples and tested for purify and yield. Two methods for removing liquid from a processing cartridge were compared: pumping and centrifugation. A sample processing cartridge was assembled as follows. A polyolefin solid support of dimensions 17.3 mm circumference and 15 mm length (American Filtrona, Richmond, Va.) was inserted into a syringe (Gilson DistriTip syringe, 1.25 ml capacity, Gilson Medical Electronics, Billiers-le-Bel, France) after removing the plunger. Previously, the solid support had been treated by saturating it with a Lysing Solution (Gentra Systems, Minneapolis, Minn.), A and then allowing it to dry. The cartridge assembly was completed by inserting a spacer, followed by a septum seal. The spacer was polypropylene tubing of 10 mm length, 5 mm outside diameter and 3 mm inside diameter. The septum was an Interlink Injection Site PN 2N3399 (Baxter Healthcare, Deerfield, Ill.) with spacer altered to allow an air-tight fit into the top of the cartridge.

The sample processing cartridge was held in a vertical position with the syringe tip at the bottom and the septum at the top. A whole blood sample of approximately 0.164 ml was aspirated into the cartridge through the syringe tip by applying negative pressure with a precision syringe pump (Cavro, Sunnyvale, Calif.). The pump was connected to the cartridge with tubing terminating in a needle which pierced the septum. The blood contacted the solid support for 2 minutes to allow for cell lysis, release of DNA, binding of the DNA to the solid support, release of RNA and digestion of the RNA by RNase. The solid support in the cartridge was washed by dispensing approximately 1.25 ml Generation DNA purification Solution® (Gentra Systems, Inc., Minneapolis, Minn.) with the syringe pump. After incubation for 1 minute, the waste solution was forced out of the cartridge by applying air pressure of approximately 3-5 psi for 10-15 seconds. The waste solution was collected in a 15 ml centrifuge tube for analysis of heme, a blood contaminant; heme content was estimated by visible spectrophotometry at 405 nm in a Beckman DU 64 spectrophotometer (Beckman Instruments, Fullerton, Calif.). This wash step was repeated four more times with the waste solution collected for each wash. Approximately 0.25 ml of a second reagent, Generation DNA Elution Solution® (Gentra Systems, Inc., Minneapolis, Minn.), was pumped into the purification cartridge through the septum. The Generation DNA Elution Solution® was held in the cartridge for 10-15 seconds and then the eluant (waste solution) was removed as described above. To monitor the efficiency of the washing steps, all five of these eluant samples were tested for the quantity of heme.

To test the efficiency of air flow vs. centrifugation to facilitate fluid removal, two additional cartridges was tested as described above except that they were washed only twice with Generation DNA Purification Solutions and once with Generation DNA Elution Solution®. To release the DNA from the solid support, a second volume of 0.25 ml of Generation DNA Elution Solution® Solution was pumped on to the sample purification cartridge, and the sample purification cartridge then placed into an enclosing heated block at 93° C. for 8 minutes. The DNA was forced out of the cartridge by applying air pressure as described above and collected in a 1.5 ml centrifuge tube. To test the DNA elution profile from the solid support, three additional DNA elutions were performed. The same experiment was repeated substituting centrifugation of the cartridge for air flow into the cartridge. The cartridge was then placed into a 15 ml tube and centrifuged at 1000×g for 2 minutes in a Mistral 1000 centrifuge (MSE, Loughborough, England). Results are calculated as follows: The % DNA was calculated by dividing the μg DNA recovered in each sample by the theoretical maximum. The μg DNA in each sample was determined by measuring UV absorbence (DU 64 spectrophotometer, Beckman Instruments, Fullerton, Calif.) at 260 nm and subtracting background absorbence at 320 nm, multiplying by the DNA extinction factor of 50, multiplying by the dilution factor and then multiplying by the volume recovered at each elution. The theoretical maximum was calculated by multiplying the number of white blood cells in the sample (7.25 million) per ml by the blood volume used (0.164 ml) then by the quantity of DNA in each cell (6 picograms). Thus the theoretical maximum quantity of DNA in a 0.164 ml volume was 7.13 μg DNA. Therefore, results are expressed as a percentage of the theoretical yield for the volume of blood treated, and are as follows.

TABLE 1

Efficiency of Contaminant Removal From DNA Purification Cartridge

| | |
|---|---|
| Eluate 1 | 86.4% Heme |
| Eluate 2 | 12.0% |
| Eluate 3 | 1.2% |
| Eluate 4 | 0.3% |
| Eluate 5 | 0.1% |
| Total = | 100% |

The results from Table 1 showed that 98.4% of heme, a major indicator of contamination in blood samples, was removed in the first two steps. Thereafter, it was concluded that only two washes with Generation DNA Purification Solutions and one with Generation DNA Elution Solutions were needed in the DNA purification procedure.

TABLE 2

Efficiency of DNA Elution From DNA Purification Cartridge Using Air Flow

| | |
|---|---|
| Eluate 1 | 33.48% |
| Eluate 2 | 24.45% |
| Eluate 3 | 24.09% |
| Eluate 4 | 15.83% |
| Total Recovered DNA = 97.85% of theoretical maximum | |

TABLE 3

Efficiency of DNA Elution From DNA Purification Cartridge Using Centrifugation

| | |
|---|---|
| Eluate 1 | 48.39% |
| Eluate 2 | 23.70% |
| Eluate 3 | 6.87% |
| Eluate 4 | 7.01% |
| Total Recovered DNA = 86% of theoretical maximum | |

Example 3

Comparison of Centrifugation Vs. Combined Mechanical Agitation and Air Flow to Elute DNA from a DNA Sample Processing Cartridge Two cartridges were prepared as described in Example 2. A well-mixed sample of whole blood (175 µl) was drawn into each cartridge using a precision syringe. The samples were subsequently drawn on to the solid supports and allowed to incubate on the solid supports for 2 minutes. After this initial cell lysis and DNA immobilization step, the column was flushed with 1.25 ml of Generation DNA Purification Solution® (Gentra Systems, Inc., Minneapolis, Minn.). The residual volume was held in the cartridge for 1 minute. After this step, the cartridges were flushed with a low pressure (approximately 3-5 psi) air stream for 10 to 15 seconds. 0.125 ml of Generation DNA Purification Solution® was added again and allowed to incubate on the solid support for one minute. The cartridges were again air flushed as described above. 750 µl of Generation DNA Elution Solution® were then added to the cartridge as a pH conditioning step. This volume was held for 10-15 seconds and the cartridge was air flushed for 5 seconds. The cartridges were then placed in an enclosing heated block at 93° C. for 5 minutes. 250 µl of preheated (90° C.) elution solution were added while the cartridge remained in the heated block at temperature. At this point a mixing step was initiated by mechanically agitating the septum with a reciprocating rod. This caused a displacement of approximately 1 mm at a frequency of approximately 5 Hertz. This secondary incubation and mixing step was continued for three minutes. At the conclusion of this step, the cartridge was air flushed and the effluent was collected. A secondary elution was performed by addition of 250 µl of elution solution followed by 5 minutes of incubation at 93° C., an air flush, and subsequent collection of the eluant. This elution step was then repeated. Results (expressed as a percentage of theoretical yield for the volume of blood treated, mean of two samples) are as follows:

First elution: 58.5%
Second elution: 14.5%
Third elution: 9.7%

A third sample was treated as the above two except that the elution steps were performed by removal of the column and centrifugal extraction in a centrifuge tube using standard manual protocols. Serial elutions were again performed. Results are as follows:

First elution: 48.4%
Second elution: 23.7%
Third elution: 6.9%

Comparison of the cartridges subjected to a combination of mechanical agitation and air flow and the cartridge subjected to centrifugation alone indicates that the efficiency of elution is relatively the same for both protocols.

Example 4

Apparatus to Purify and Isolate DNA

An apparatus is designed to implement the automated and integrated loading, purification, isolation and collection of nucleic acids. This apparatus enables efficient use of the sample processing cartridges described in example 1. Samples (whole blood or other defined fluids) are processed in sample processing cartridges as described in example 1. The apparatus is designed to provide mechanical and fluidic communication between the sample processing cartridge, control units, reagent containers, flow systems, heating chambers and heating elements, sample processing containers, sample collection containers, waste removal systems, etc. All required reagents are carried on board the system in specially designed vessels. The apparatus is provided with an appropriate waste containment system. The apparatus is designed to work with a Lysing Solution Generation DNA Purification Solution® (Gentra Systems, Inc., Minneapolis, Minn.) & Generation Elution Solution (Gentra Systems, Inc., Minneapolis, Minn.). This apparatus in all its embodiments provides automated DNA extraction in the low to medium volume market segments, defined here as 20 to 1000 samples per day.

4.1 Possible System Configurations

The apparatus can be configured in three basic system configurations. These are as follows:

(i) Core System (CS): A highly automated system with essentially continuous operation;
(ii) Low throughput system (LTS): A low throughput system providing an automated batch operation; and
(iii) Enhanced throughput system (ETS): An enhanced throughput system with highly automated and continuous operations and with added resources providing a higher processing rate.

4.2. Samples 4.2. a Sample Processing Capabilities (i) Core System (CS)

A running rate of at least 60 samples per hour after an initial lag time not to exceed 20 minutes. This rate is sustainable until depletion of on board reagents, samples and sample containers. A provision can be made to allow replenishment of samples and purified DNA containers with minimal impact on throughput.

(ii) Low Throughput System (LTS)

Allows a batch process of 20 purified DNA samples with a total elapsed time not to exceed 45 minutes.

(iii) Enhanced Throughput System (ETS)

Permits a running rate of 100-150 samples per hour after an initial lag time not to exceed 20 minutes. This rate is sustainable until depletion of on board reagents, samples and sample containers. A provision can be made to allow replenishment of samples and purified DNA containers with minimal impact on throughput. The ETS is limited, however, to samples of 300 μL or less.

4.2. b Sample Containers

The system processes samples from at least one defined draw tube or a defined sample cup. The operator removes the cap or cover before loading the instrument.

4.2. c Samples Allowed

The apparatus is designed to process whole blood or other defined fluids containing no particulate matter larger than 50μ. Specimen removal is essentially from the top surface of the fluid.

4.2. d Sample Aspiration

The system is capable of aspirating samples in volumes ranging from 20 to 100 μL (300 μL ETS) with an imprecision of not more than 5% at any allowed volume. Delivery of samples to the solid support have a margin of error of not greater than 10% for volumes less than 50 μL, and not greater than 7.5% for volumes greater than 50 μL. The system is designed such that cross contamination between samples is non-detectable.

4.2. e Sample Loading Capacity

Core System and Enhanced Throughput System 20 samples may be loaded at one time. Provision shall be made for placement of additional samples as processing proceeds.

Low Throughput System

No provision for placement of additional samples until run is completed.

4.2. f Samples of Purified and Isolated Nucleic Acids

The apparatus is designed to transfer 20 to 1000 μL (300 μL ETS) nominal volume with a CV not to exceed 25% for volumes below 50 μL, not to exceed 15% for volumes greater than 50 μL. The systems are designed such that no cross contamination occurs.

Core System and Enhanced Throughput System

A minimum of three defined purified DNA containers of differing volumes can be supported. Desirably, these containers can be mixed and matched to required purified DNA volumes within a run. A minimum capacity of 20 purified DNA containers will be provided. Provision shall be made for removal of purified DNA and placement of additional containers as processing proceeds. Provision shall be made to allow incorporation of alternative purified DNA containers (e.g. 96 well plates) with appropriate hardware and software changes.

Low Throughput System

No provision for removal of purified DNA until run is complete. No provision for collection containers other than those contained on the sample rotor.

4.3 Reagents

Purification Solution: The apparatus is designed to deliver volumes of 20 to 1000 μL (300 μL ETS) as required the defined protocol. Capacity adequate for 500 samples (approximately one day's supply) is provided. Purification solution is provided in containers suitable for direct use on the instrument via cap removal and replacement with a ported camp captive to the instrument. Automatic means to monitor solution level is desired, but not required.

Elution Solution: The apparatus is designed to deliver volumes of 20 to 1000 μL (300 μL ETS) as required the defined protocol. Capacity adequate for 500 samples (approximately one day's supply) is provided. Elution solution is provided in containers suitable for direct use on the instrument via cap removal and replacement with a ported cap captive to the instrument. Automatic means to monitor solution level is desired, but not required.

Cleaning solutions: Unless required for routine processing, cleaning solutions are placed into reagent positions as needed by the operator. If required for routine processing a dedicated location can be provided.

4.4 Waste and Waste Containment

Liquid Wastes

Liquid wastes will be contained in a suitable container providing ready access to the user. Liquid wastes shall be considered biohazards and the waste collection system will be constructed to minimize potential exposure. The liquid waste collection and containment system(s) will be constructed to ensure no detectable cross contamination of samples or purified DNA. Reusable containers adequate for processing 500 samples (approximately one day's usage) are supplied. Means are provided to alert the user to empty the container. This is enabled by a level detection device coupled to a control system that triggers an alarm warning the operator.

Solid Wastes

Solid waste is anticipated to be limited to spent cartridges. Solid wastes shall be considered biohazards and the waste collection system will be constructed to minimize potential exposure. The solid waste collection and containment system will be constructed to ensure no detectable cross contamination of samples or purified DNA. Disposable containers (a bio-hazard bag or equivalent) adequate for processing 500 samples (approximately one day's usage) are provided. Means are provided to alert the user to empty the container. This is enabled by a level detection device coupled to a control system that triggers an alarm warning the operator.

4.5 Cartridges

Four cartridges types can be accommodated by the system. These will differ in sample volume capacity. A range from 20 μL to 1000 μL will be provided, specific volumes are 20, 100, 250 and 1000 μL. Each cartridge will contain a pretreated solid support and will be provided with a tip suitable for direct aspiration of sample from either the defined sample cup or a standard (uncapped) drawtube. The cartridge will be constructed of materials verified to be non-interfering with the immediate chemistry and will contribute no leachables (ionic, non-ionic, metals, etc.) which may interfere with downstream processes.

Core System and Enhanced Throughput System

The on board instrument accessible inventory is a minimum of 96 cartridges. A mix of cartridge sizes can be supported in three blocks of 32 each. Each block contains only cartridges of the same volume capacity.

4.6 Performance Characteristics

User Interface

Means will be provided to allow input of sample ID and protocol requirements (volumetric variations only, choice of 3) for each sample. Specimen and purified DNA ID via barcode will be supported. An LIS interface will be provided. The LTS will have a minimal interface and may not include LIS or positive sample ID.

Mixing

Core System and Enhanced Throughput System

If it is determined that mixing is required to provide adequate cell suspension due to settling during time spent in the inlet queue, means shall be provided to obtain uniform suspension of cells.

Thermal Performance

The apparatus is capable of heating sample processing cartridges and contents thereof to a temperature of 90° C.±5° C. within ten minutes. Prior to initiation of this heating cycle, solid support and associated fluid temperatures should not exceed ambient temperature ±10° C.

There are no specific requirement for purified nucleic acid temperatures as delivered to the sample container. On board reagents have no special thermal handling requirements. These will be in uncontrolled areas, but temperatures shall not exceed ambient ±10° C.

4.7 Initial Set-Up of the System

The system is designed to initially prompt the operator to verify the following variables:

(i) Number of samples;
(ii) Number of sample processing containers;
(iii) Number of sample collection containers;
(iv) reagent volumes; and
(v) waste container levels.

The operator can then enter process requests using manual input keys, or can enter a programmed algorithm designed by the operator for the task at hand, or alternately avail of several downloadable programs. The process requests specify the volume of each sample required to be processed and match it either to a barcode identification code or the position of the sample on the sample station. In one embodiment, this sample station is a rotor or turntable tray designed to hold sample containers. The system will determine if adequate inventory of reagents is present. If an adequate supply of reagents is not present, the system will prompt the user to replenish the required supplies.

4.8 Sample or Specimen Loading

The samples are stored in sample containers that are placed in a sample station. The sample containers are either uncapped drawtubes or defined sample cups; the sample station is a sample rotor or turntable device. The operator will load the uncapped drawtubes or defined sample cups to a removable sample or specimen rotor. If these containers are provided with an appropriate bar code, the system will read the codes for identification and tracking purposes. The user will fill a sample rotor with empty sample vials. If these vials are identified with bar coding, the system will deliver the processed purified DNA into the matching vial. If no bar coding is provided, the system will deliver processed purified DNA to the position on the purified DNA rotor corresponding to the sample rotor position.

After preparing the rotors, the user will place them into the corresponding system positions. At this point the system will read barcodes if present and commence processing. During processing, additional samples may be added if rotor space permits. An interrupt feature will be provided for this action. If no rotor space is available, additional samples may be added when the initial sample rotor has been processed. The system will inform the operator when the purified DNA rotor will be available for removal and replacement. If the purified DNA rotor has not been replaced prior to arrival of additional processed purified DNA, the system will cease accepting additional samples and will sound a mutable audible alarm. In process samples will continue processing and those purified DNA ready for elution will be held in the system until purified DNA vials are available.

4.9 Processing of Samples and Product

The system will determine the appropriate cartridge for each sample based on the information provided by operator. A multifunction sampling arm will select the cartridge from an on board inventory. The arm will establish fluidic communication with the interior of the cartridge as well as a mechanical connection. After acquisition, the arm will index the cartridge to the sample tube and aspirate the required volume into the cartridge. Fluid level sensing will be provided to allow the system to determine when the aspiration tip of the cartridge has contacted the sample and to minimize contamination of the exterior of the cartridge. After aspiration, the arm will transport the loaded cartridge to a purification of the sample occur in the process rotor. After processing, a multifunction arm will remove the cartridge from the process rotor, dispense the purified DNA into the appropriate vial on the purified DNA rotor and dispose of the spent cartridge in a waste container.

4.10 Operational Sequence for Low Throughput System

The Low Throughput system will contain all liquid reagents required for sample processing, but no cartridge inventory will be provided. The user will load samples and empty sample vials to a combined sample/sample rotor. Sample vials and purified DNA will be physically matched to allow the operator to maintain identification. Data input will be similar to that described for the core system. The operator will load process cartridges directly to the process rotor. The process rotor will be essentially identical in function to that contained on the core system. After loading of samples, purified DNA vials and cartridges sample transfer and processing proceeds as for the core system with the following exceptions. A single multifunction arm will reacquire the cartridge, elute the purified DNA to the proper purified DNA vial and dispose of the spent cartridge. No additional samples may be loaded until all processing is complete.

Example 5

Purification of Nucleic Acid in Whole Blood and Cultured Cells Using a Cellulose Acetate Solid Support Matrix A cartridge was constructed using a standard 1 mL polypropylene syringe (Catalog Number 309602, Beckton Dickinson, Franklin Lakes, N.J.) into which was inserted a solid support. The solid support was comprised of cellulose acetate (Filtrona®, American Filtrona, Richmond, Va.) of dimensions about 5 mm diameter×27 mm long. The solid support had been treated previously with 500 µL Basic Lysing Reagent and RNase A and allowed to dry at room temperature for 24 hours. The Basic Lysing reagent contained 0.5% SDS, 0.1 M Tris, 0.1 M EDTA to which was added 0.04 mg/ml RNase A (about 100 units RNase A per mg). Two whole blood samples and two K562 cultured cells samples each containing about 2 million cells in a 300 µL volume were each pipetted into a cartridge supported in a vertical position. The cartridges were supported in a rigid manifold which is placed in a chamber that can be heated to the appropriate reaction temperature via a programmable heating element. The cartridges were then set in place using a cartridge clasp holder and attached to a reagent port through which Generation DNA purification Solution® (Gentra Systems, Inc., Minneapolis, Minn.) (the wash solution) or Generation DNA Elution Solution® (Gentra Systems, Inc., Minneapolis, Minn.) (the elution solution) can be delivered through a 2-way valve. After incubating for 15 minutes at room temperature to allow the cells to lyse and the RNase to digest RNA present in the samples, a 300 μl aliquot of Generation DNA purification Solution® was introduced via 2.5 mm i.d. silicon tubing using a 60 rpm peristaltic pump (Catalog No. MC 13003 Markson Science, Hillsboro, Oreg.). After a 1 minute incubation, gas was pumped through the cartridge to expel the cartridge contents into a waste container. Then, a second 300 μL volume of Generation DNA purification Solution® was pumped into the cartridge and incubated for 1 minute. This washing step was repeated once more for a total of three washes with Generation DNA purification Solution®. The solid support in the cartridge was rinsed with 300 μL of Generation DNA Elution Solution®. To remove the purified nucleic acid from the solid support, 300 μL of Generation DNA Elution Solution® was pumped into the cartridge. The cartridge was incubated at 60° C. for 30 minutes and the Generation DNA Elution Solution®, which contained the purified nucleic acid, was pumped out of the cartridge and into a standard 1.5 mL microcentrifuge tube.

To evaluate the purified DNA samples in an amplification assay, an aliquot of 5 μL was removed from each supernatant fraction and added to 45 μL PCR amplification solution. Each amplification reaction contained 1× amplification buffer (Promega, Madison, Wis.), 1.5 mM $MgCl_2$, 200 μM each deoxynucleotide, 2.5 units Taq Polymerase (Promega, Madison, Wis.), and 1 μM each primer. Oligonucleotide primers given by Ridker et al., *New Engl. J. Med.* 1995; 332:912-917, were used to amplify a factor V gene sequence during 35 cycles, where a cycle was defined as 94° C. for 1 minute, 58° C. for 1 minute, and 72° C. for 1 minute. A 10 μl aliquot from each DNA sample was electrophoresed through a 2% agarose gel at 80 Volts for 45 minutes to determine amplification results. The gel and running buffer contained 0.125 μg per mL ethidium bromide to allow visualization of the amplified DNA on a transilluminator.

A factor V amplification product of 223 base pairs was observed for each of the three wet blood samples and for each of the three dry blood samples. These results showed that the liquid phase purification method of the present invention gave substantially pure DNA from both wet and dry whole blood samples.

The patent applications incorporated by reference herein may be used in conjunction with the present invention, for example, in the washing or elution of the sample/solid support, to perform PCR or other processing on the isolated nucleic acid, to incorporate a specific solid support, or for other uses apparent to one of ordinary skill in the art.

Example 6

Sample Processing Cartridge with Inlet Ports and Breakaway Seals

Figure 11:
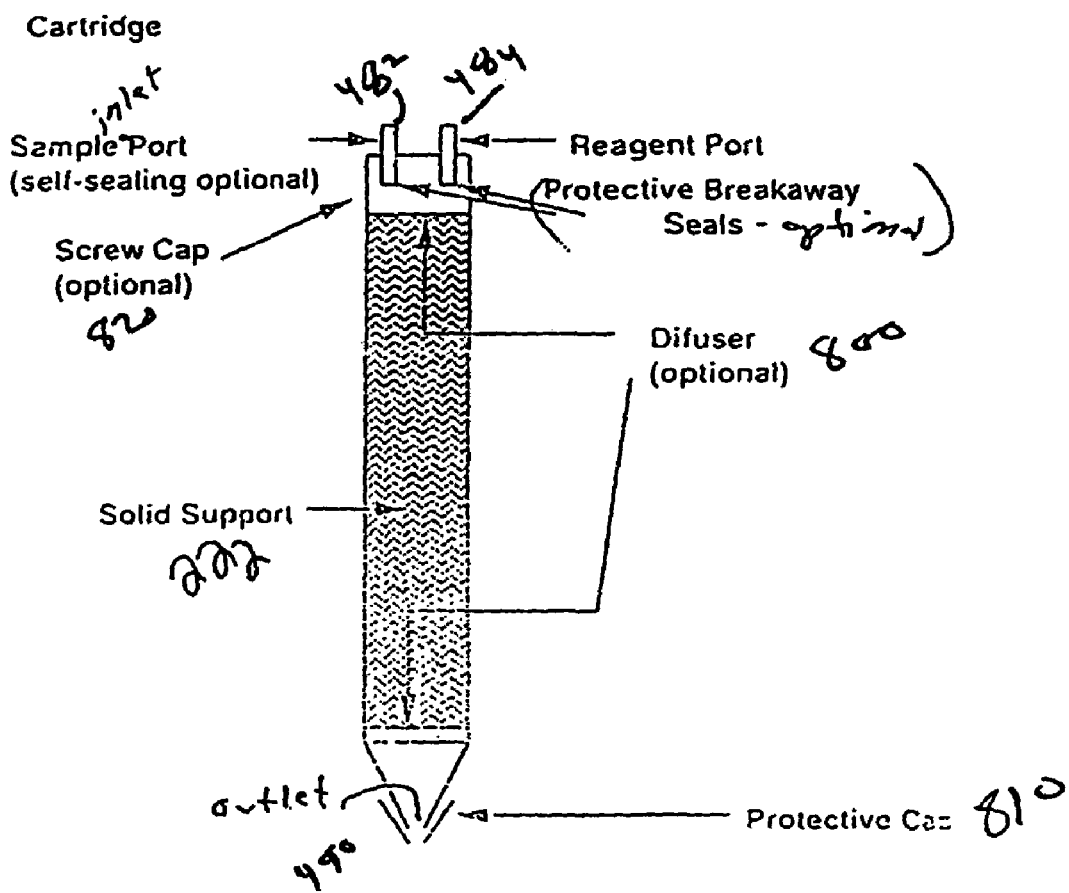
FIG. 11 shows an embodiment of a sample processing cartridge with breakaway seals.

FIG. 11 shows one embodiment of a sample processing container that may be used to purify and isolate nucleic acids. As shown, the cartridge 680 contains the solid support 222 (as well as the sample), an optional diffuser 800 (to restrict the flow of fluid through the cartridge), a protective cap 810 (for use when the cartridge outlet port is not connected), an outlet port 490, and an optional screw cap 820. Separate inlet ports 482, 484 may be provided for the sample 482 and for the reagents 484 (wash solution and elution solution) and the sample inlet port 482 may be self sealing.

The cartridge 680 of FIG. 11 is built of a rugged material and is able to process samples to achieve a high volume of isolated nucleic acid.

Example 7

A Sample Collection Container

Figure 12:
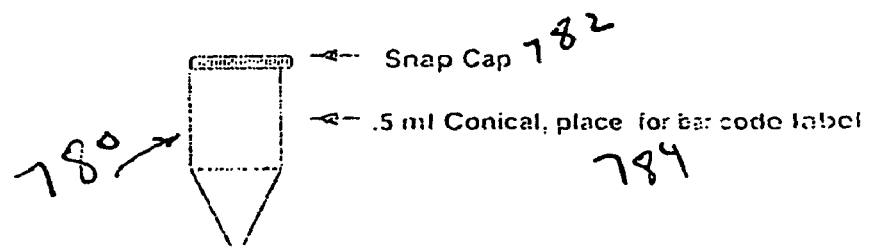
FIG. 12 shows an embodiment of a sample collection tube.

FIG. 12 shows the sample collection tube 780 which may be placed in a sample collection platform of an apparatus to purify and isolate nucleic acids. The sample collection tube 780 has a removable snap cap 782 (for transportation of the sample) and an area 784 to affix a machine identifiable identification code, including a bar code, or a label or both.

Example 8

Sample Processing Cartridge with a Perforated Basket

Figure 10:
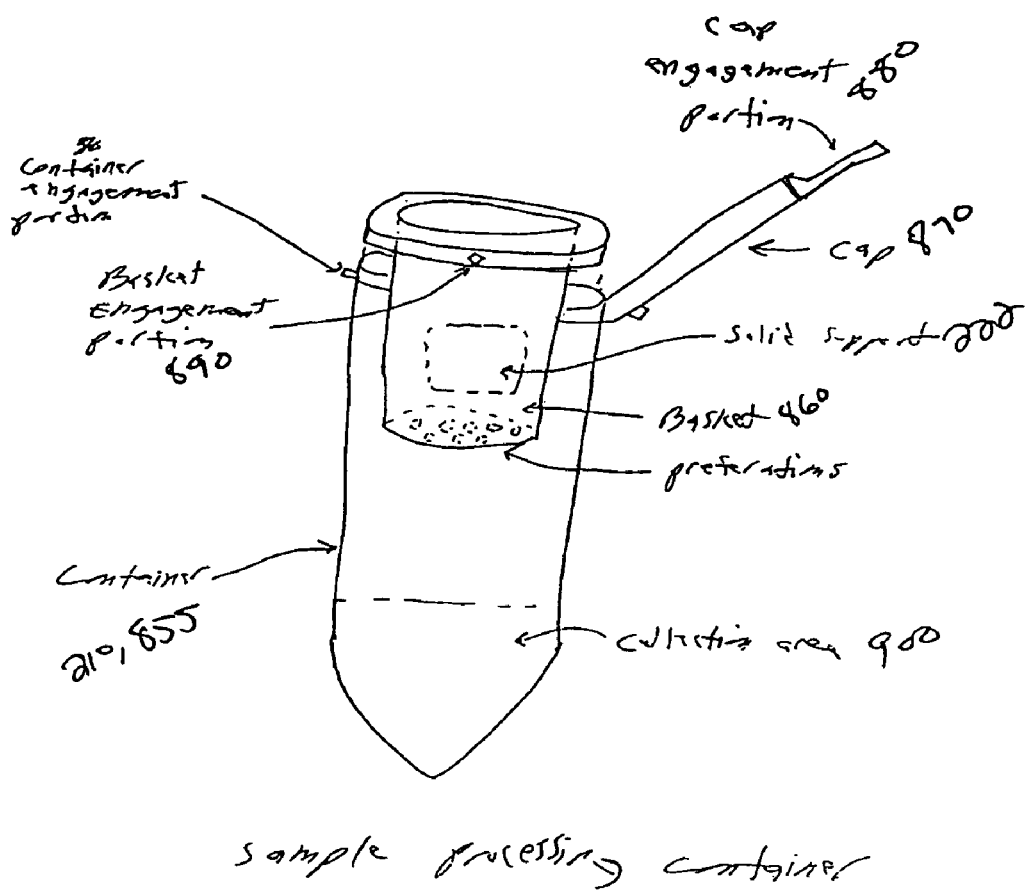
FIG. 10 shows an embodiment of a sample processing container for a centrifuge/microfuge apparatus for use in the present invention.

FIG. 10 shows a sample processing container 210, 855 used in the centrifuge/microfuge embodiment of the present invention. As shown in FIG. 10, a solid support 222 is placed within a basket 860. The basket is perforated at least on one side in order to allow impurities to be washed off of the solid support 222. The basket 860 is held within the sample processing container 855 which has a collection area 900. The collection area holds the impurities which are washed off of the solid support 222 and passed through the perforations. The sample processing container 855 may be sealed and unsealed using, for example, a cap 870. The cap has a cap engagement portion 880 allowing an automated apparatus to engage and open the cap. The basket also has a basket engagement portion 890 so that the basket may be manipulated by the automated apparatus. The basket engagement portion 890 may be a notch or indentation on opposite sides of the basket 860 which allow prongs from the automated apparatus to engage the basket 860 and hold the basket 860 in place.

This sample processing container may be centrifuged in the following way. First, the sample and solid support 222 are loaded into the basket 860. The basket 860 is loaded into the sample processing container 855, and wash solution applied. The cap 870 is then closed and the sample processing carrier 800 is centrifuged, for example, for about 20 seconds, causing impurities to collect in the collection area 900. The application of wash solution and centrifugation is repeated as many time as necessary to ensure that most of the impurities are removed.

The cap 870 is then opened, and the basket 860 grasped or supported (for example by a robotic arm, not shown). The sample processing container 855 having waste collected in its collection area is removed and the basket 860 placed into clean sample processing container 855. Elution solution is then added to the solid support 222. The cap 870 is then closed and the sample is centrifuged (preferably after heating to 90° C.) to collect the isolated nucleic acid in the collection area 900. When the basket 860 is removed from the sample processing container 855 a suitable sample of nucleic acid is available for further processing.

Example 9

Design of an Automated Apparatus to Implement DNA Purification and Isolation

An automated system 2000 to implement the integrated loading, purification, isolation and collection of a sample containing nucleic acids is designed. This automated system is designed with the intent to purify nucleic acids from a variety of solid supports, sample processing containers. Specifically, it may be used to purify DNA that has been purified and isolated on the sample processing cartridge of example 1. Schematic diagrams of the automated system are provided in FIGS. 8a, 8b, and 8c.

Figure 8A:
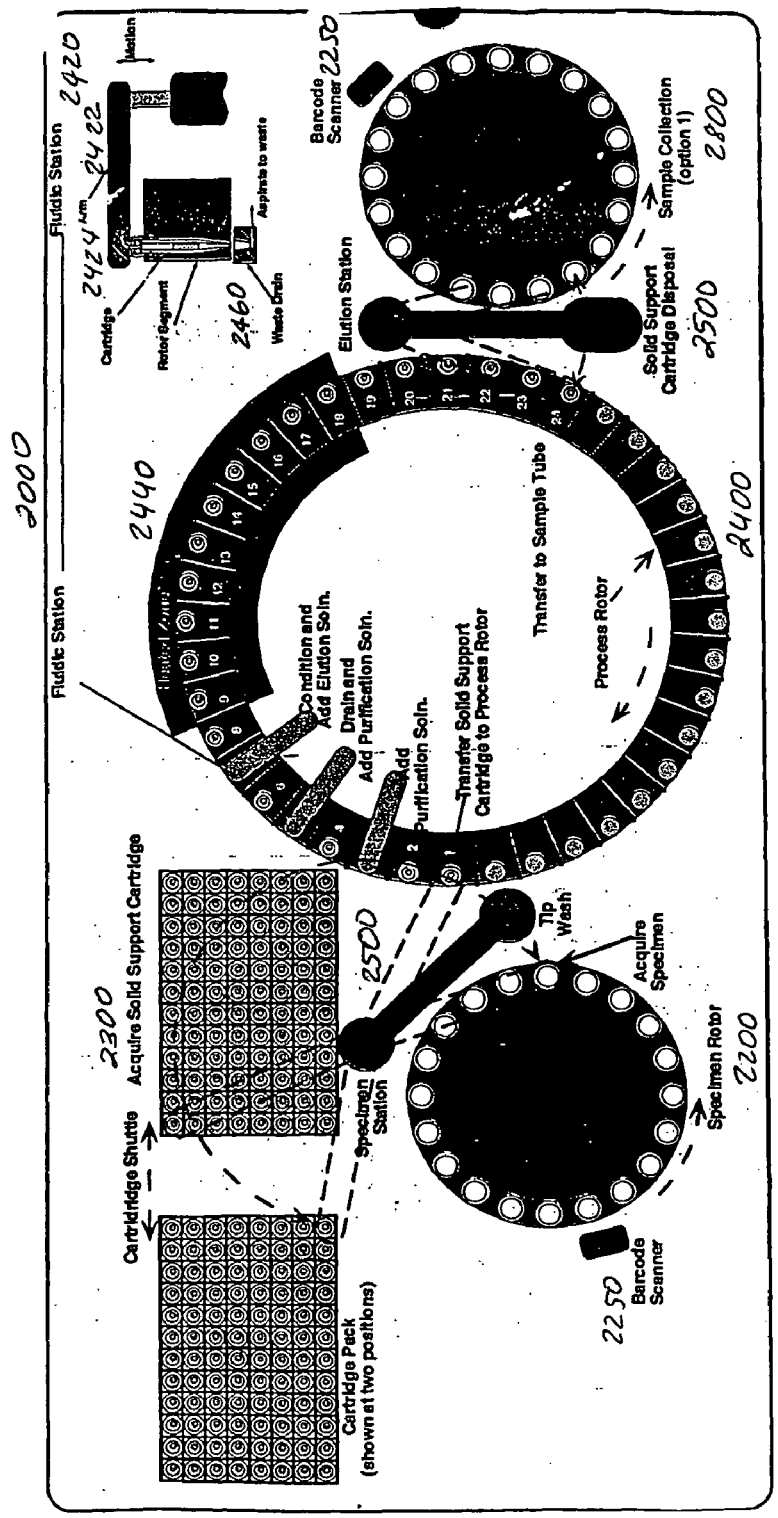
FIGS. 8a, 8b, and 8c show representative examples of an automated apparatus for isolating nucleic acid.
Figure 8B:
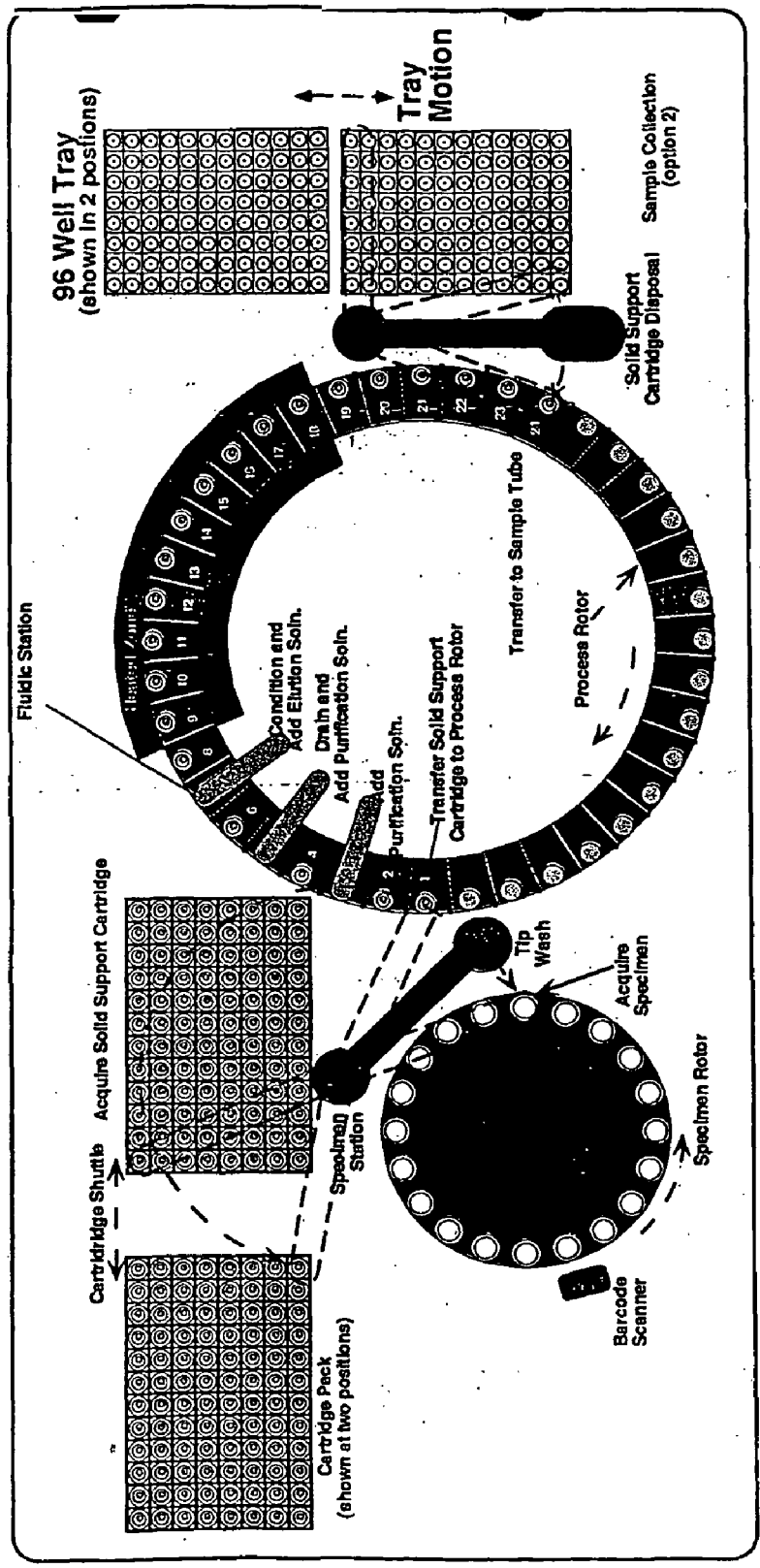
Figure 8C:
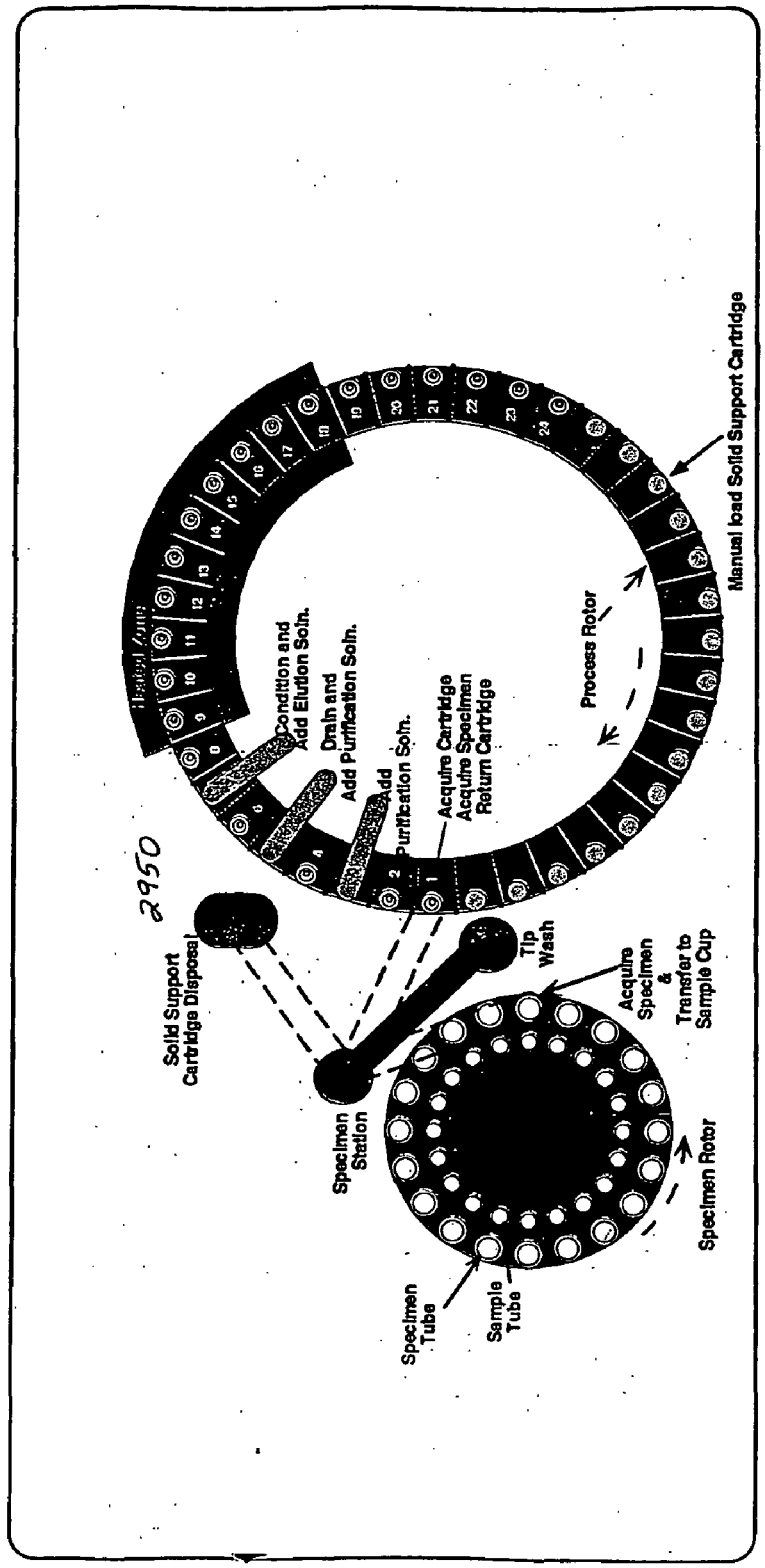

The general elements of this system are:

9.1. Sample or Specimen Station 2200: This station may be a platform that is stationary or capable of linear or rotational motion. Preferably, it is a rotor 2200 or turntable as shown in FIGS. 8a, 8b and 8c. Optionally, the station is controlled by a control mechanism and is equipped with a scanning device capable of scanning a mechanically identifiable identification code on each sample or specimen container. The scanning device comes equipped with a sensor that may be mechanical, electrical, electromagnetic, etc. In a preferred embodiment, the scanning sensor is a barcode sensor 2250. The station may be microprocessor controlled and may communicate with a central control station or computer via necessary circuitry.

9.2 Cartridge Storage Station 2300: This station provides access to onboard inventory of cartridges. It consists essentially of one or more platforms or sample processing container carriers that hold the sample processing containers. The platforms may be a rectangular platform with individual spaces to hold the cartridges. One embodiment of a cartridge storage station is a standard 96-well plate with wells deep enough to hold the individual cartridges, or a suitably designed cartridge pack 2300. The station may be automated to allow the rapid and efficient processing of more than one platform or sample processing container carriers. The stations are shuttled to the appropriate loading point as required. Optionally, the station is controlled by a control mechanism and is equipped with a scanning device capable of scanning a mechanically identifiable identification code on each sample or specimen container. The scanning device comes equipped with a sensor that may be mechanical, electrical, electromagnetic, etc. The station may be microprocessor controlled and may communicate with a central control station or computer via necessary circuitry.

9.3 Processing Station 2400: The processing station consists of a process rotor 2400 designed to transport the sample processing carriers containing the sample through the required fluidic stations 2420 and provides heat as required during the elution steps using a heated zone 2440. Each fluidic station may be come equipped with a heating mechanism if desired. The heated zone 2440 may be heated using a heating coil, convection heat, a hot water bath, etc. A schematic diagram of a fluidic station is provided in FIG. 9. The fluidic station consists of a mechanical arm 2422 capable of vertical and horizontal motion. The arm supports the required fluid circuitry by which wash solution for purification and elution solution for elution of nucleic acids from the solid support can be delivered. It may also be equipped with tubing through which a vacuum may be applied to the sample processing cartridge. At the free end of the mechanical arm 2422 of the fluidic station 2420 a specially designed fluidic connection 2424 allows the sample processing cartridge to maintain a hermetic seal with the external fluid circuit and the vacuum tubing. The fluidic station 2420 further consists of a waste station 2460 specially designed to drain waste solutions which are then aspirated to a waste container as shown in FIG. 9. The waste station allows for effective aerosol containment.

9.4 Purified sample collection station 2800: This station consists of a purified sample collection rotor 2800 as shown in FIG. 8a or at least one purified sample collection tray 2850 as shown in FIG. 8b. One embodiment of the purified sample collection tray 2850 is a 96 well plate.

9.5 Positioning or Loading Arm 2500: Samples and sample processing containers may be positioned or loaded using an automated pivoting arm designed to pivot to a fixed position in the Cartridge Storage Station 2300, grip a sample processing cartridge 1000, penetrate the septum 1200 at the top of the sample processing cartridge with a cannula attached to the fluid control circuit, transport the cartridge to the patient sample contained in a sample container in the sample station 2200, establish electrical connection with the cartridge to enable use of a capacitive level sense circuit, and deliver the cartridge to the sample processing rotor 2400. Alternately, the arm may grip the sample processing cartridge 1000 and simply deliver it to the processing rotor 2400. The sample is then delivered to the sample processing cartridge 1000 via a pumping or pipetting mechanism. FIGS. 8a, 8b and 8c show two different embodiments of the use of loading arm 2500. In FIGS. 8a and 8b the loading arm 2500 pivots to the cartridge storage station 2300, then to the sample rotor 2200 where it aspirates a sample, and finally loads the sample processing cartridge with the sample into the processing station 2400. In FIG. 8c the loading arm 2500 is designed to acquire a sample from a sample container in a specially designed sample station 2200, transfer the sample via aspiration, pipetting or pumping to a sample cup, then acquire a sample processing cartridge 1000 that has been manually loaded by the operator on the sample processing rotor 2400, move it to the sample station where it acquires the sample from the sample cup, and finally move the sample processing cartridge 1000 back to the sample processing rotor 2400. In yet another embodiment of the invention, the loading arm 2500 can pivot and dispose of the sample processing cartridge into a cartridge disposal area 2950.

A second loading arm 2500 may be used to dispense the final product, i.e, the purified and isolated nucleic acid from the sample processing cartridge 1000 after purification and isolation to either a purified sample collection station consisting of a purified sample collection rotor 2800 as shown in FIG. 8a or at least one purified sample collection tray 2850 as shown in FIG. 8b. One embodiment of the purified sample collection tray 2850 is a 96 well plate. A shuttling mechanism can position one or more of the purified sample collection trays 2850. The purified sample collection rotor 2800 may be scanned using a similar scanning device as that contained on the sample rotor 2200. This may be a barcode sensor 2250. Once the rotating arm 2500 dispenses the final product into the purified sample collection station, it pivots and returns the sample processing cartridge to the sample processing motor 2400.

9.6 Fluid circuitry to perform all required fluid motions and transfers: This would include precision pumps (computer controlled syringe pumps for example) vacuum or other waste system, pressurized air for displacement of fluids.

Figure 2:
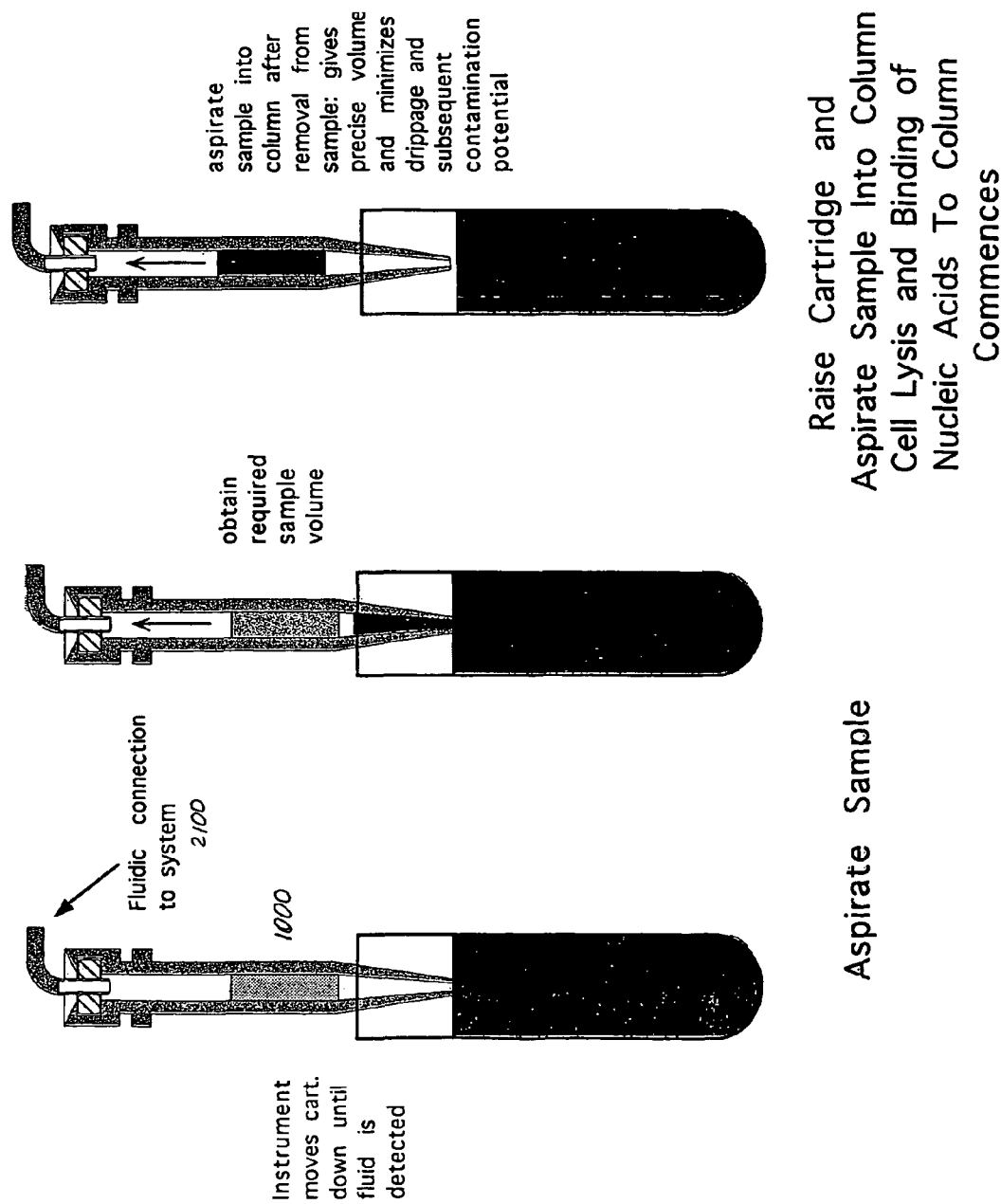
FIG. 2 shows a representative example of a sample, sample processing container and sample container as used in the loading step of the present invention.

This apparatus allows a process comprising the following steps:

Aspiration of the sample: See FIG. 2

Figure 3:
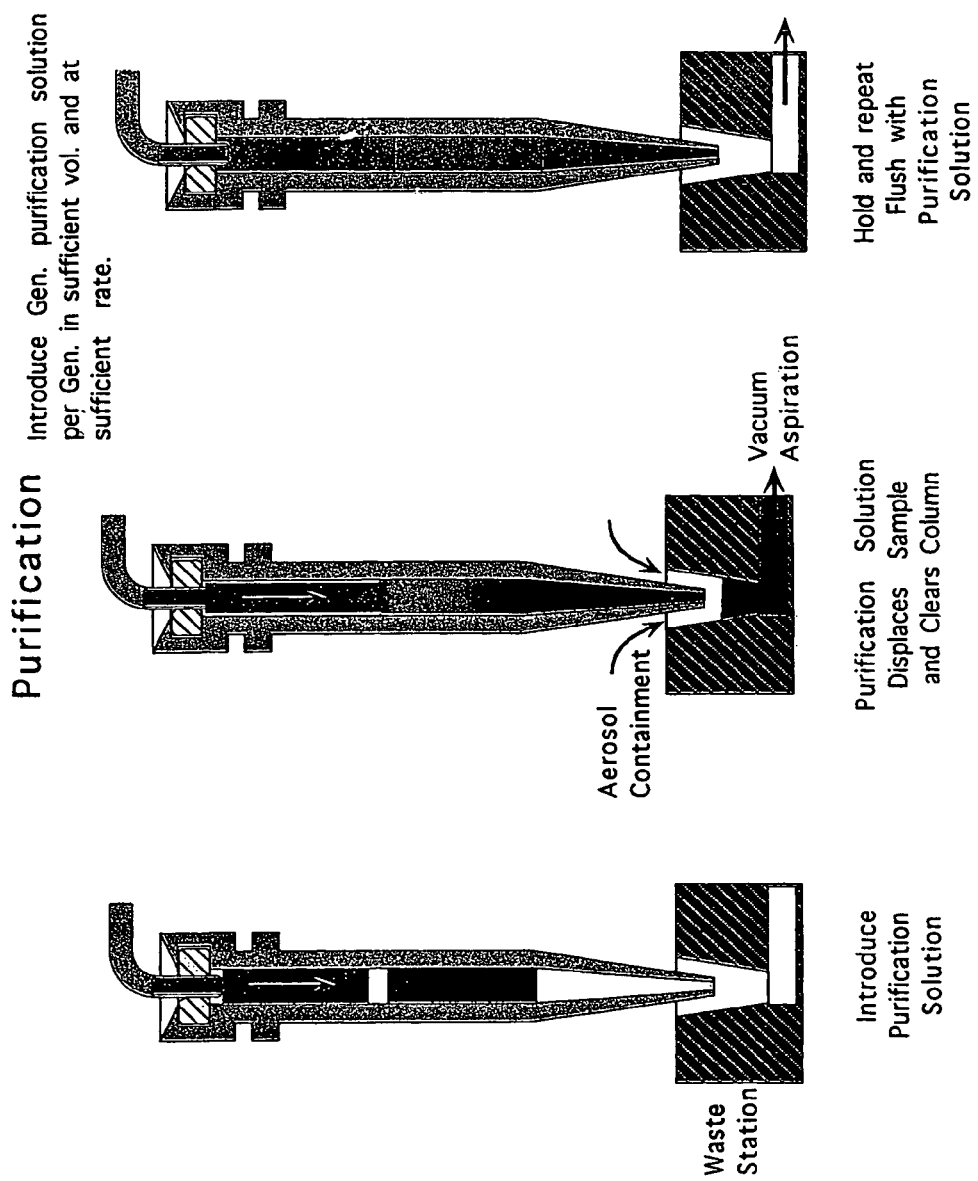
FIG. 3 shows a representative example of the sample, sample processing container containing the solid support, and wash solution as used in the purifying step of the present invention.

Purification of the sample: See FIG. 3

Flushing and conditioning the Sample Processing Cartridge: See FIG. 4

Figure 5A:
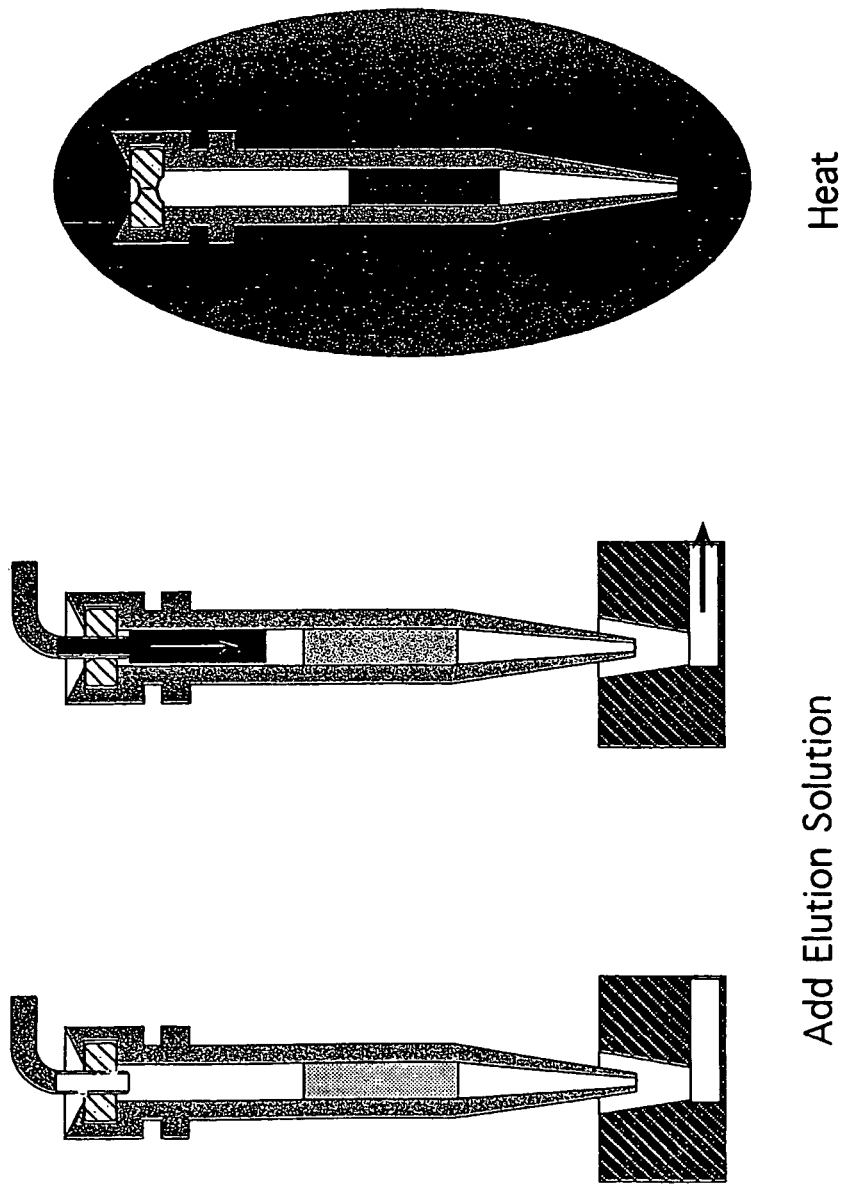
FIG. 5a) shows a representative example of optional process of heating the sample solid support, sample processing container, and elution solution in the isolating step of the present invention.

Optional heating and elution: See FIG. 5a

Inducing fluid motion of a bolus of elution solution: FIG. 5b

Dispensing and collecting the purified and isolated sample: FIG. 6

Figure 7:
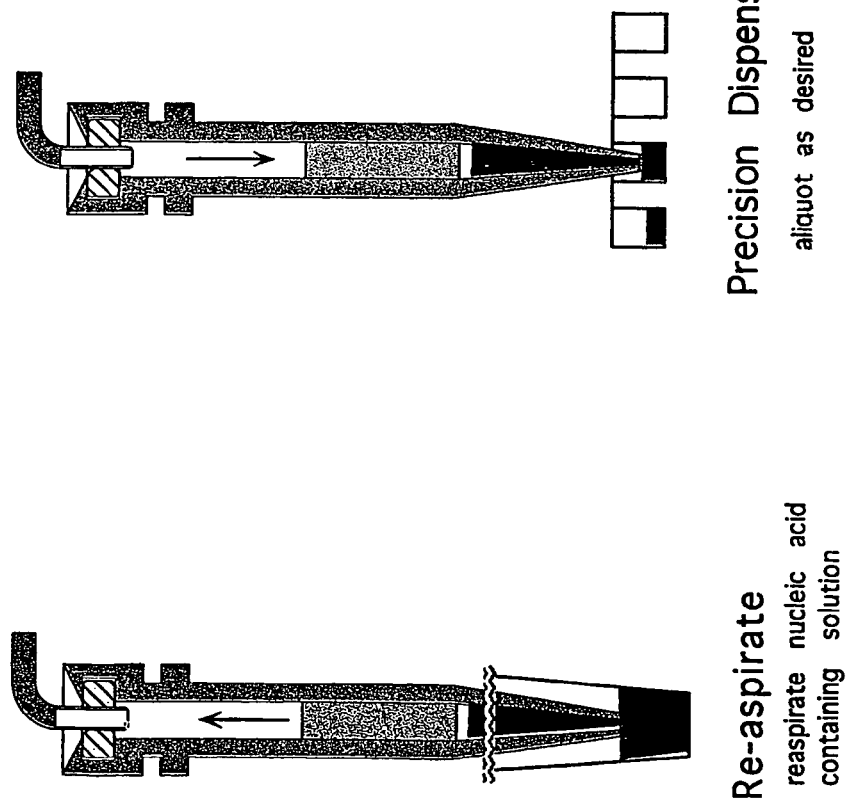
FIG. 7 shows a representative example of an optional step of dispensing a precision aliquot of nucleic acid solution.

Optional step of creating precision aliquots: FIG. 7

The foregoing description of the present invention has been presented for purposes of illustration and description. Furthermore, the description is not intended to limit the invention to the specific embodiments described. Consequently, variations and modifications commensurate with the above teachings, and within the skill and knowledge of the relevant art, are part of the scope of the present invention. The embodiments described herein above are intended to enable others skilled in the art to utilize the invention in the disclosed, or other related embodiments and with various modifications required by the particular application or use. It is intended that the appended claims be construed to include alternative embodiments to the extent permitted by law.

What is claimed is:

1. A method for isolating a nucleic acid comprising:
    introducing a fluid sample containing the nucleic acid into a sample processing container through an outlet of the sample processing container;
    introducing a purification/wash solution into the sample processing container through the outlet of the sample processing container;
    forcing the purification/wash solution out of the sample processing container;
    introducing an elution solution into the sample processing container; and
    forcing the elution solution out of the sample processing container, thereby isolating the nucleic acid.

2. The method of claim 1, further comprising heating the sample processing container after introducing the fluid sample.

3. The method of claim 2, wherein the heating is by microwaves or ultrasound waves.

4. The method of claim 1, further comprising introducing a lysing solution into the sample processing container.

5. The method of claim 1, wherein the elution solution is introduced into the outlet of the sample processing container.

6. The method of claim 1, wherein the elution solution is introduced into the inlet of the sample processing container.

7. The method of claim 1, wherein the fluid sample is selected from the group consisting of body fluids, body wastes, body excretions, and blood.

8. The method of claim 1, wherein the forcing is performed by vacuum pressure, positive pressure, gravity, centrifugation, or mechanical agitation.

9. The method of claim 1, wherein the fluid sample is mixed with the purification/wash solution and elution solution by the induction of fluid motion through the solid support by alternately dispensing and aspirating the purification/wash solution and elution solution through the septum.

* * * * *